United States Patent
Wogoman et al.

(10) Patent No.: US 10,537,445 B2
(45) Date of Patent: Jan. 21, 2020

(54) SURGICAL INSTRUMENTS FOR PREPARING A PATIENT'S TIBIA TO RECEIVE AN IMPLANT

(71) Applicant: DEPUY IRELAND UNLIMITED COMPANY, Cork OT (IE)

(72) Inventors: Thomas E. Wogoman, Warsaw, IN (US); Jon M. Edwards, Warsaw, IN (US); Matthew S. Wallace, Warsaw, IN (US); Jeremy Oden, Huntington, IN (US); Corinna Johanna Klawon, San Rafael, CA (US); Megan Wallace, Warsaw, IN (US); Erica Roche, Warsaw, IN (US)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 235 days.

(21) Appl. No.: 14/886,923

(22) Filed: Oct. 19, 2015

(65) Prior Publication Data
US 2017/0105849 A1 Apr. 20, 2017

(51) Int. Cl.
*A61F 2/46* (2006.01)
*A61F 2/38* (2006.01)
(Continued)

(52) U.S. Cl.
CPC ........ *A61F 2/4684* (2013.01); *A61B 17/1735* (2013.01); *A61B 17/1764* (2013.01);
(Continued)

(58) Field of Classification Search
CPC .......... A61F 2/4684; A61F 2/389; A61F 2/38; A61F 2002/30616; A61F 2/461; A61F 2002/4205; A61F 2/3886; A61F 2/30734
See application file for complete search history.

(56) References Cited

U.S. PATENT DOCUMENTS

| 4,135,517 A | 1/1979 | Reale et al. |
| 4,211,228 A | 7/1980 | Cloutier |

(Continued)

FOREIGN PATENT DOCUMENTS

| EP | 1219269 A1 | 7/2002 |
| EP | 1415625 A2 | 5/2004 |

(Continued)

OTHER PUBLICATIONS

Zimmer NexGen LCCK, Surgical Technique for use with LCCK 4-in-1 Instrument, 2009, 52 pages.
(Continued)

*Primary Examiner* — Ann Schillinger
(74) *Attorney, Agent, or Firm* — Barnes & Thornburg LLP

(57) ABSTRACT

An orthopaedic surgical instrument system that includes an orthopaedic surgical instrument adapted to be positioned on a proximal end of a patient's tibia, and a tibial bearing trial assembly, and a tibial evaluation component, and a tibial base trial component configured to be coupled to the orthopaedic surgical instrument. A tibial evaluation component includes a base plate and a generally Y-shaped posterior buttress extending upwardly from a superior surface of the base plate, such that the posterior buttress of the insert component is configured to be received in the opening of the tibial bearing trial assembly to prevent rotation of the tibial bearing trial component relative to the tibial base trial component.

13 Claims, 15 Drawing Sheets

(51) Int. Cl.
  *A61F 2/30* (2006.01)
  *A61B 17/17* (2006.01)
  *A61B 17/00* (2006.01)

(52) U.S. Cl.
  CPC ....... *A61B 2017/0046* (2013.01); *A61F 2/389* (2013.01); *A61F 2/3859* (2013.01); *A61F 2002/30331* (2013.01); *A61F 2002/30492* (2013.01); *A61F 2002/30495* (2013.01); *A61F 2002/4624* (2013.01)

(56) References Cited

U.S. PATENT DOCUMENTS

| | | |
|---|---|---|
| 4,378,607 A | 4/1983 | Wadsworth |
| D269,547 S | 6/1983 | Rosenthal |
| 4,659,331 A | 4/1987 | Matthews et al. |
| 4,938,769 A | 7/1990 | Shaw et al. |
| 4,944,757 A | 7/1990 | Martinez et al. |
| 5,019,103 A | 5/1991 | Van Zile et al. |
| 5,047,058 A | 9/1991 | Roberts et al. |
| 5,152,797 A | 10/1992 | Luckman et al. |
| 5,197,488 A | 3/1993 | Kovacevic et al. |
| D338,270 S | 8/1993 | Stephens et al. |
| 5,306,276 A | 4/1994 | Johnson et al. |
| 5,344,458 A | 9/1994 | Bonutti et al. |
| 5,356,414 A | 10/1994 | Cohen et al. |
| 5,364,401 A | 11/1994 | Ferrante et al. |
| 5,387,241 A | 2/1995 | Hayes et al. |
| 5,464,406 A | 11/1995 | Ritter et al. |
| 5,470,354 A | 11/1995 | Hershberger et al. |
| 5,472,415 A | 12/1995 | King et al. |
| 5,486,178 A | 1/1996 | Hodge |
| 5,514,143 A | 5/1996 | Bonutti et al. |
| 5,540,696 A | 7/1996 | Booth et al. |
| 5,569,260 A | 10/1996 | Petersen |
| 5,569,263 A | 10/1996 | Hein et al. |
| 5,597,379 A | 1/1997 | Haines et al. |
| 5,601,565 A | 2/1997 | Huebner |
| 5,607,431 A | 3/1997 | Dudasik et al. |
| 5,611,802 A | 3/1997 | Samuelson et al. |
| 5,613,970 A | 3/1997 | Houston et al. |
| 5,643,272 A | 7/1997 | Haines et al. |
| 5,649,928 A | 7/1997 | Grundei |
| 5,683,469 A | 11/1997 | Johnson et al. |
| 5,690,636 A | 11/1997 | Wildgoose et al. |
| 5,702,464 A | 12/1997 | Lackey et al. |
| 5,704,941 A | 1/1998 | Jacober et al. |
| 5,709,689 A | 1/1998 | Ferrante et al. |
| 5,716,361 A | 2/1998 | Masini et al. |
| 5,720,752 A | 2/1998 | Elliott et al. |
| 5,733,292 A | 3/1998 | Gustilo et al. |
| 5,735,904 A | 4/1998 | Pappas |
| 5,749,876 A | 5/1998 | Duvillier et al. |
| 5,766,261 A | 6/1998 | Neal et al. |
| 5,769,854 A | 6/1998 | Bastian et al. |
| 5,776,200 A | 7/1998 | Johnson et al. |
| 5,776,201 A | 7/1998 | Colleran et al. |
| 5,782,925 A * | 7/1998 | Collazo ................ A61F 2/4684 623/20.28 |
| 5,788,700 A | 8/1998 | Morawa et al. |
| 5,792,143 A | 8/1998 | Samuelson et al. |
| 5,860,969 A | 1/1999 | White et al. |
| 5,860,980 A | 1/1999 | Axelson, Jr. et al. |
| 5,860,982 A | 1/1999 | Ro et al. |
| 5,928,286 A | 7/1999 | Ashby et al. |
| 5,935,128 A | 8/1999 | Carter et al. |
| 5,941,884 A | 8/1999 | Corvelli et al. |
| 5,976,147 A | 11/1999 | Lasalle et al. |
| 5,989,261 A | 11/1999 | Walker et al. |
| 6,022,377 A | 2/2000 | Nuelle et al. |
| 6,024,746 A | 2/2000 | Katz et al. |
| 6,080,196 A | 6/2000 | Bertin |
| 6,090,144 A | 7/2000 | Letot et al. |
| 6,102,953 A | 8/2000 | Huebner |
| 6,102,955 A | 8/2000 | Mendes et al. |
| 6,106,529 A | 8/2000 | Techiera |
| 6,159,216 A * | 12/2000 | Burkinshaw ....... A61B 17/1735 606/88 |
| 6,193,758 B1 | 2/2001 | Huebner |
| 6,214,052 B1 | 4/2001 | Burkinshaw |
| 6,277,123 B1 | 8/2001 | Maroney et al. |
| 6,344,043 B1 | 2/2002 | Pappas |
| 6,355,045 B1 | 3/2002 | Gundlapalli et al. |
| 6,478,799 B1 | 11/2002 | Williamson |
| 6,485,521 B1 | 11/2002 | Say et al. |
| 6,641,614 B1 | 11/2003 | Wagner et al. |
| 6,660,039 B1 | 12/2003 | Evans et al. |
| 6,663,636 B1 | 12/2003 | Lin |
| 6,673,114 B2 | 1/2004 | Hartdegen et al. |
| 6,702,824 B2 | 3/2004 | Maroney et al. |
| 6,712,824 B2 | 3/2004 | Millard et al. |
| 6,723,097 B2 | 4/2004 | Fraser et al. |
| 6,736,852 B2 | 5/2004 | Callaway et al. |
| 6,743,258 B1 | 6/2004 | Keller |
| 6,746,487 B2 | 6/2004 | Scifert et al. |
| 6,821,470 B2 | 11/2004 | Gundlapalli et al. |
| 6,827,723 B2 | 12/2004 | Carson |
| 6,827,739 B2 | 12/2004 | Griner et al. |
| 6,916,324 B2 | 7/2005 | Sanford et al. |
| 6,923,817 B2 | 8/2005 | Carson et al. |
| D518,178 S | 3/2006 | Christiansen |
| 7,104,996 B2 | 9/2006 | Bonutti |
| 7,105,026 B2 | 9/2006 | Johnson et al. |
| 7,135,044 B2 | 11/2006 | Bassik et al. |
| 7,141,067 B2 | 11/2006 | Jones et al. |
| 7,247,169 B1 | 7/2007 | Lo et al. |
| 7,291,174 B2 | 11/2007 | German et al. |
| 7,309,363 B2 | 12/2007 | Dietz |
| 7,338,496 B1 | 3/2008 | Winslow et al. |
| 7,338,499 B1 | 3/2008 | Kuczynski et al. |
| 7,344,541 B2 | 3/2008 | Haines et al. |
| 7,435,263 B2 | 10/2008 | Barnett et al. |
| 7,632,283 B2 | 12/2009 | Heldreth |
| 7,632,314 B2 | 12/2009 | Dietz |
| 7,634,306 B2 | 12/2009 | Sarin et al. |
| 7,658,767 B2 | 2/2010 | Wyss |
| 7,683,812 B2 | 3/2010 | Lewin |
| 7,691,150 B2 | 4/2010 | Cronin et al. |
| 7,695,519 B2 | 4/2010 | Collazo |
| 7,699,853 B2 | 4/2010 | Durand-Allen et al. |
| 7,731,755 B2 | 6/2010 | Wyss et al. |
| D619,251 S | 7/2010 | Justiniano-Garcia et al. |
| 7,837,690 B2 | 11/2010 | Metzger |
| 7,854,737 B2 | 12/2010 | Daniels et al. |
| 7,959,635 B1 | 6/2011 | Bonutti |
| 7,963,969 B2 | 6/2011 | Sanford |
| 8,012,215 B2 | 9/2011 | Metzger et al. |
| 8,029,574 B2 | 10/2011 | Kellar et al. |
| 8,052,758 B1 | 11/2011 | Winslow |
| 8,065,927 B2 | 11/2011 | Crottet et al. |
| 8,066,777 B2 | 11/2011 | Palmer et al. |
| 8,070,752 B2 | 12/2011 | Metzger et al. |
| 8,070,823 B2 | 12/2011 | Kellar et al. |
| 8,092,545 B2 | 1/2012 | Coon et al. |
| 8,105,387 B2 | 1/2012 | Barnett et al. |
| 8,109,942 B2 | 2/2012 | Carson |
| 8,128,705 B2 | 3/2012 | Birkbeck et al. |
| 8,133,282 B2 | 3/2012 | Hushka et al. |
| 8,137,358 B2 | 3/2012 | Winslow et al. |
| 8,141,437 B2 | 3/2012 | Amirouche et al. |
| 8,142,512 B2 | 3/2012 | Brooks et al. |
| 8,187,283 B2 | 5/2012 | Thomas |
| 8,197,489 B2 | 6/2012 | Chessar et al. |
| 8,197,549 B2 | 6/2012 | Amirouche et al. |
| 8,231,631 B2 | 7/2012 | Lavallee et al. |
| D666,713 S | 9/2012 | Waite et al. |
| 8,287,547 B2 | 10/2012 | Martin et al. |
| 8,357,166 B2 | 1/2013 | Aram et al. |
| 8,403,993 B2 | 3/2013 | Aram et al. |
| 8,414,653 B2 | 4/2013 | Burstein et al. |
| 8,419,740 B2 | 4/2013 | Aram et al. |
| 8,425,615 B2 | 4/2013 | Berelsman et al. |
| 8,435,304 B2 | 5/2013 | Dietz |
| 8,480,677 B2 | 7/2013 | Groh |

(56) References Cited

U.S. PATENT DOCUMENTS

| | | |
|---|---|---|
| 8,491,589 B2 | 7/2013 | Fisher et al. |
| 8,491,664 B2 | 7/2013 | McMahon et al. |
| 8,498,711 B2 | 7/2013 | Roche |
| 8,506,571 B2 | 8/2013 | Chana et al. |
| 8,529,578 B2 | 9/2013 | Daniels et al. |
| 8,535,382 B2 | 9/2013 | Kehres et al. |
| 8,551,179 B2 | 10/2013 | Jones et al. |
| 8,568,485 B2 | 10/2013 | Ries et al. |
| 8,585,710 B2 | 11/2013 | Fischer et al. |
| 8,585,711 B2 | 11/2013 | Klotz et al. |
| 8,591,593 B2 | 11/2013 | Metzger |
| 8,597,358 B2 | 12/2013 | Landry et al. |
| 8,603,101 B2 | 12/2013 | Claypool et al. |
| 8,617,250 B2 | 12/2013 | Metzger |
| 8,764,827 B2 | 7/2014 | Steinhardt |
| 8,979,847 B2 | 3/2015 | Belcher et al. |
| 2001/0053935 A1 | 12/2001 | Hartdegen et al. |
| 2002/0082607 A1* | 6/2002 | Heldreth ............ A61B 17/1735 606/102 |
| 2004/0039450 A1 | 2/2004 | Griner et al. |
| 2004/0097951 A1 | 5/2004 | Steffensmeier |
| 2004/0186583 A1 | 9/2004 | Keller |
| 2004/0225368 A1 | 11/2004 | Plumet et al. |
| 2005/0075640 A1 | 4/2005 | Collazo et al. |
| 2006/0069447 A1 | 3/2006 | DiSilvestro et al. |
| 2006/0089641 A1 | 4/2006 | Collazo |
| 2006/0111790 A1 | 5/2006 | Dietz |
| 2006/0184176 A1* | 8/2006 | Straszheim-Morley ..................... A61B 17/1764 606/88 |
| 2007/0233137 A1 | 10/2007 | Seo et al. |
| 2007/0239165 A1 | 10/2007 | Amirouche |
| 2008/0091273 A1 | 4/2008 | Hazebrouck |
| 2008/0114464 A1 | 5/2008 | Barnett et al. |
| 2008/0119938 A1 | 5/2008 | Oh |
| 2008/0147075 A1 | 6/2008 | Bonutti |
| 2008/0154270 A1 | 6/2008 | Haines et al. |
| 2008/0221569 A1 | 9/2008 | Moore et al. |
| 2008/0269901 A1 | 10/2008 | Baynham et al. |
| 2009/0076514 A1 | 3/2009 | Haines |
| 2009/0082773 A1 | 3/2009 | Haines |
| 2009/0084491 A1 | 4/2009 | Uthgenannt et al. |
| 2009/0125114 A1 | 5/2009 | May et al. |
| 2009/0138018 A1 | 5/2009 | Haines |
| 2009/0216325 A1 | 8/2009 | May et al. |
| 2009/0240254 A1* | 9/2009 | Arnhold ................. A61F 2/461 606/99 |
| 2009/0265013 A1 | 10/2009 | Mandell |
| 2010/0010635 A1 | 1/2010 | Straszheim-Morley et al. |
| 2010/0016979 A1 | 1/2010 | Wyss et al. |
| 2010/0063594 A1 | 3/2010 | Hazebrouck et al. |
| 2010/0076438 A1 | 3/2010 | Correia et al. |
| 2010/0082111 A1 | 4/2010 | Thomas |
| 2010/0125337 A1 | 5/2010 | Grecco et al. |
| 2010/0298941 A1 | 11/2010 | Hes et al. |
| 2010/0305711 A1 | 12/2010 | McKinnon et al. |
| 2011/0066246 A1* | 3/2011 | Ries .................. A61B 17/1764 623/20.27 |
| 2011/0178605 A1 | 7/2011 | Auger et al. |
| 2012/0041566 A1 | 2/2012 | Lenz et al. |
| 2012/0158152 A1 | 6/2012 | Claypool et al. |
| 2012/0209391 A1 | 8/2012 | Cipolletti et al. |
| 2012/0226481 A1 | 9/2012 | Carson |
| 2012/0239160 A1 | 9/2012 | Belew et al. |
| 2012/0259339 A1 | 10/2012 | Hood et al. |
| 2012/0259421 A1 | 10/2012 | Satterthwaite et al. |
| 2012/0265317 A1 | 10/2012 | Metzger |
| 2012/0323334 A1 | 12/2012 | Jones et al. |
| 2013/0006252 A1 | 1/2013 | Waite, II et al. |
| 2013/0006253 A1 | 1/2013 | Waite, II et al. |
| 2013/0006370 A1 | 1/2013 | Wogoman et al. |
| 2013/0006371 A1 | 1/2013 | Wogoman et al. |
| 2013/0006376 A1 | 1/2013 | Wogoman et al. |
| 2013/0006377 A1 | 1/2013 | Waite, II et al. |
| 2013/0013075 A1 | 1/2013 | Fisher et al. |
| 2013/0013077 A1 | 1/2013 | Metzger et al. |
| 2013/0020733 A1 | 1/2013 | Berger |
| 2013/0024001 A1 | 1/2013 | Wentorf et al. |
| 2013/0030538 A1 | 1/2013 | Metzger et al. |
| 2013/0046385 A1 | 2/2013 | Hartdegen et al. |
| 2013/0079671 A1 | 3/2013 | Stein et al. |
| 2013/0096567 A1 | 4/2013 | Fisher et al. |
| 2013/0103153 A1 | 4/2013 | Blackwell et al. |
| 2013/0103160 A1 | 4/2013 | Young |
| 2013/0173011 A1 | 7/2013 | Otto et al. |
| 2013/0184834 A1 | 7/2013 | Brooks et al. |
| 2013/0190885 A1 | 7/2013 | Ammann et al. |
| 2013/0204267 A1 | 8/2013 | Dietz |
| 2013/0204377 A1 | 8/2013 | Samuelson et al. |
| 2013/0211531 A1 | 8/2013 | Steines et al. |
| 2013/0245769 A1 | 9/2013 | Gimbel et al. |
| 2013/0245803 A1 | 9/2013 | Lang |
| 2013/0261505 A1 | 10/2013 | Sherman et al. |
| 2013/0261758 A1 | 10/2013 | Claypool et al. |
| 2013/0261759 A1 | 10/2013 | Claypool et al. |
| 2013/0282132 A1 | 10/2013 | White et al. |
| 2013/0289569 A1 | 10/2013 | Wilkinson |
| 2013/0289726 A1 | 10/2013 | Curran et al. |
| 2013/0304221 A1 | 11/2013 | Blaylock et al. |
| 2014/0039636 A1 | 2/2014 | Kurtz |
| 2014/0052269 A1 | 2/2014 | Claypool et al. |
| 2014/0066934 A1 | 3/2014 | Deirmengian et al. |
| 2014/0081412 A1 | 3/2014 | Metzger |
| 2014/0155902 A1 | 6/2014 | Sikora et al. |
| 2014/0156017 A1 | 6/2014 | Salyer |
| 2014/0159282 A1 | 6/2014 | Smith et al. |
| 2014/0172112 A1 | 6/2014 | Marter |
| 2014/0276858 A1 | 9/2014 | Major et al. |
| 2014/0277539 A1* | 9/2014 | Cook ..................... A61F 2/30 623/20.32 |

FOREIGN PATENT DOCUMENTS

| | | | |
|---|---|---|---|
| EP | 1415625 A3 | 5/2004 | |
| EP | 1415625 B1 | 5/2006 | |
| EP | 1836997 A1 | 9/2007 | |
| EP | 2168537 A1 | 3/2010 | |
| EP | 2168537 B1 | 11/2011 | |
| EP | 2540256 A1 | 1/2013 | |
| GB | 2323037 A | 9/1998 | |
| WO | 9925263 A1 | 5/1999 | |
| WO | 0013597 A1 | 3/2000 | |
| WO | 2008024836 A2 | 2/2008 | |
| WO | 2008054389 A1 | 5/2008 | |
| WO | 2008024836 A3 | 7/2008 | |
| WO | 2011073632 A1 | 6/2011 | |

OTHER PUBLICATIONS

DePuy Orthopaedics, Inc., Sigma Revision and M.B.T. Revision Tray, Surgical Technique, 2008, 82 pages.

Smith & Nephew, Legion, Revision Knee System, Surgical Technique, 2005, 40 pages.

Biomet, Vanguard SSK, Revision System, Surgical Technique, Feb. 2008, 64 pages.

GMK Revision, Surgical Technique, Ref. 99.27.12US rev. 1, 1999, 74 pages.

PFC Sigma RP-F, Specialist 2 Instruments, Surgical Technique, Performance in Flexion, 2007, 32 pages.

P.F.C. Sigma Rotating Platform Knee System with M.B.T Tray, Primary Procedure with a Curved or Posterior Stablised Implant, 2003, 43 pages.

LCS High Performance Instruments, Surgical Technique, 2008, 44 pages.

Sigma High Performance Instruments, Design Rationale, 2007, 12 pages.

Sigma High Performance Instruments, Classic Surgical Technique, 2010, 52 pages.

Coordinate Ultra Revision Knee System, Surgical Technique, 1997, p. 24.

(56) References Cited

OTHER PUBLICATIONS

P.F.C. Sigma Knee System, Revision, Surgical Technique, 2000, pa. 66.
Sigma Revision and M.B.T. Revision Tray, Surgical Technique, 2012, p. 84.
S-Rom Noiles Rotating Hinge, Surgical Technique, 2012, p. 76.
European Search Report for European Application No. 12174178.9-2310, dated Sep. 6, 2012, 6 pages.
Partial European Search Report, European Application No. 16194469.9-1664, dated Mar. 2, 2017, 8 pages.
Extended European Search Report, European Application No. 16194469.9-1664 / 3158953, dated Jun. 22, 2017, 13 pages.
European Search Report, European Application No. 13175055.6-1654, dated Sep. 16, 2013, 5 pages.

\* cited by examiner

SURGICAL INSTRUMENTS FOR PREPARING A PATIENT'S TIBIA TO RECEIVE AN IMPLANT

CROSS-REFERENCE

Cross-reference is made to U.S. patent application Ser. No. 14/886,796, now U.S. Pat. No. 10,195,056, entitled "METHOD FOR PREPARING A PATIENT'S TIBIA TO RECEIVE AN IMPLANT" by Thomas E. Wogoman et al. and filed on Oct. 19, 2015, U.S. patent application Ser. No. 13/530,771, now U.S. Pat. No 8,986,390, entitled "METHOD OF TRIALING A KNEE PROSTHESIS" by Thomas E. Wogoman et al. and filed on Jun. 22, 2012, U.S. patent application Ser. No. 13/530,662, now U.S. Pat. No. 8,951,301, entitled "METHOD OF USING A TRIALING SYSTEM FOR A KNEE PROSTHESIS" by Thomas E. Wogoman et al. and filed on Jun. 22, 2012, U.S. patent application Ser. No. 13/530,649, now U.S. Pat. No. 8,968,412, entitled "TRIALING SYSTEM FOR A KNEE PROSTHESIS AND METHOD OF USE" by Thomas E. Wogoman et al. and filed on Jun. 22, 2012, and U.S. patent application Ser. No. 14/265,960, now U.S. Pat. No. 9,861,491, entitled "TIBIAL TRIAL SYSTEM FOR A KNEE PROSTHESIS" by David W. Waite et al. and filed on Apr. 30, 2014, each of which is hereby incorporated by reference.

TECHNICAL FIELD

The present disclosure relates generally to orthopaedic surgical instruments and, more particularly, to surgical instruments used with a patient's tibia.

BACKGROUND

Joint arthroplasty is a well-known surgical procedure by which a diseased and/or damaged natural joint is replaced by a prosthetic joint. A typical knee prosthesis includes a patella prosthetic component, a tibial tray, a femoral component, and a polymer insert or bearing positioned between the tibial tray and the femoral component. Femoral components are designed to be attached to a surgically-prepared distal end of a patient's femur. Tibial trays are designed to be attached to a surgically-prepared proximal end of a patient's tibia.

To facilitate the replacement of the natural joint with the knee prosthesis, orthopaedic surgeons use a variety of orthopaedic surgical instruments such as, for example, prosthetic trial components, cutting blocks, drill guides, milling guides, and other surgical instruments. Prosthetic trial components, such as, for example, a femoral trial component and a tibial bearing trial component, are used to size and select the components of the knee prosthesis that will replace the patient's natural joint. A procedure that utilizes the trial components to size and select the components of the knee prosthesis is often referred to as a trial reduction.

SUMMARY

According to one aspect of the disclosure, an orthopaedic surgical instrument system for use during a surgical procedure to implant an orthopaedic knee prosthesis is disclosed. The system includes a tibial base trial component adapted to be positioned on a surgically-prepared proximal end of a patient's tibia, an insert component shaped to be received in an opening defined in the tibial base trial component, and a tibial bearing trial component having an inner sidewall that defines an opening therein. The insert component comprises a base plate and a generally Y-shaped posterior buttress extending upwardly from a superior surface of the base plate. The posterior buttress of the insert component is configured to be received in the opening of the tibial bearing trial component to prevent rotation of the tibial bearing trial component relative to the tibial base trial component.

In some embodiments, the posterior buttress may include a post positioned adjacent to a posterior edge of the base plate and a pair of arms extending posteriorly from the post and outwardly from the posterior edge of the base plate.

In some embodiments, the pair of arms may include a first arm and a second arm. A first imaginary line may extend along a lateral-most edge of the first arm of the posterior buttress. A second imaginary line may extend along a medial-most edge of the second arm of the posterior buttress and intersect the first imaginary line to define an angle of intersection therebetween. The angle of intersection may be between 45-145°.

Additionally, in some embodiments, the insert component may further comprise an anterior buttress extending outwardly from an anterior edge of the base plate. The anterior buttress may include a pair of arms extending anteriorly from the anterior edge of the base plate and a tab extending superiorly from an anterior end of each arm.

In some embodiments, the system may include a retention mechanism to secure the insert component to the tibial base trial component. The retention mechanism may comprise an annular rim extending outwardly from the base plate of the insert component, and a groove defined in the tibial base trial component sized to receive the annular rim of the insert component.

In some embodiments, the insert component may include a first prong extending medially from the base plate and a second prong extending laterally from the base plate. Additionally, in some embodiments, the insert component may include a keel configured to extend inferiorly and outwardly from the opening in the tibial base trial component when the insert component is received in the opening defined in the tibial base trial component.

In some embodiments, the tibial base trial component may include an inferior surface positioned opposite the superior surface. The opening in the tibial base trial component may be defined by an inner wall extending inwardly from the superior surface to a shelf surface positioned between the superior surface and the inferior surface. A number of fixation pinholes may extend through a posterior section of the shelf surface and the inferior surface.

In some embodiments, the system may also comprise a fixation pin including a head including an inferior surface configured to engage the posterior section of the shelf surface and a superior surface positioned opposite the inferior surface. The fixation pin may also include a shaft extending from the inferior surface of the head that is sized to extend inferiorly from at least one of the fixation pinholes defined in the tibial base trial component. When the inferior surface of the head of the fixation pin is engaged with the posterior section of the shelf surface, the superior surface of the head of the fixation pin may be configured to be positioned at or below an imaginary plane defined by the superior surface of the tibial base trial component.

In some embodiments, the system may comprise a pin extraction tool comprising a stationary member, a pivoting member pivotally coupled to the handle, and a receiving end including a first jaw extending from the stationary member and a second jaw extending from the pivoting member. The first jaw and the second jaw may be configured to engage the head of the fixation pin. The pivoting member is pivotable between a closed position in which the first jaw and the second jaw define a pocket sized to retain the head of the fixation pin, and an open position in which the first jaw and the second jaw are spaced apart to permit the head of the fixation pin to be disengaged from the first jaw and the second jaw.

In some embodiments, the insert component may be a first insert component. The system may further comprise a second insert component configured to be separately received in the opening defined in the tibial base trial component in place of the first insert component. The second insert component may have a central post, and a superior surface of the central post may have a ramp surface defined therein. The ramp surface may incline superiorly in an anterior-to-posterior direction.

According to another aspect, an orthopaedic surgical instrument system for use during a surgical procedure to implant an orthopaedic knee prosthesis comprises a tibial base trial component including a superior surface, an inferior surface positioned opposite the superior surface that is adapted to be positioned on a surgically-prepared proximal end of a patient's tibia, an opening being defined by an inner wall extending inwardly from the superior surface to a shelf surface positioned between the superior surface and the inferior surface, and a number of fixation pinholes extending through a posterior section of the shelf surface and the inferior surface of the tibial base trial component. The system also comprises an insert component shaped to be received in the opening defined in the tibial base trial component, and a tibial bearing trial component having an inner sidewall that defines an opening therein. The insert component comprises a base plate and a posterior buttress extending upwardly from a superior surface of the base plate. The posterior buttress of the insert component is configured to be received in the opening of the tibial bearing trial component to prevent rotation of the tibial bearing trial component relative to the tibial base trial component.

In some embodiments, the insert component may further comprise an anterior buttress extending outwardly from an anterior edge of the base plate. Additionally, in some embodiments, the anterior buttress of the insert component may include a pair of arms extending anteriorly from the anterior edge of the base plate and a tab extending superiorly from an anterior end of each arm.

In some embodiments, the insert component may be a first insert component of a plurality of insert components. Each insert component may be shaped to be separately received in the opening defined in the tibial base trial component. A number of the insert components may include a base plate and a keel extending inferiorly from the base plate. Additionally, in some embodiments, the keel may include a pair of spikes extending inferiorly from the base plate.

According to another aspect, an orthopaedic surgical instrument system comprises a tibial base trial component including a superior surface, an inferior surface positioned opposite the superior surface that is adapted to be positioned on a surgically-prepared proximal end of a patient's tibia, an opening being defined by an inner wall extending inwardly from the superior surface to a shelf surface positioned between the superior surface and the inferior surface, and a fixation pinhole extending through a posterior section of the shelf surface and the inferior surface of the tibial base trial component. The system also comprises a fixation pin including a head and a shaft extending inferiorly from the head that is sized to be received in the fixation pinhole of the tibial base trial component, an insert component shaped to be received in the opening defined in the tibial base trial component, and a tibial bearing trial component adapted to be positioned on the insert component. The head of the fixation pin is sized to be at or below the superior surface of the tibial base trial component when the head is engaged with the shelf surface.

In some embodiments, the system may further comprise a surgical instrument including a pair of jaws configured to selectively engage the head of the fixation pin, the pair of jaws comprising a first jaw including a semi-circular flange and a second jaw including an arced flange extending less than 180 degrees.

According to another aspect of the disclosure, a method of trialing prosthetic components of a knee prosthesis is disclosed. The method comprises positioning a tibial base trial component on a surgically-prepared proximal end of a patient's tibia, positioning a femoral trial component on a surgically-prepared distal end of a patient's femur, inserting an insert component into an opening defined in the tibial base trial component, advancing a first fixation pin into a posterior fixation pinhole defined in the tibial base trial component, positioning a tibial bearing trial component over the insert component, between the tibial base trial component and the femoral trial component, and moving the patient's tibia between extension and flexion with the femoral trial component engaged with the tibial bearing trial component such that the tibial base trial component rotates on the proximal end of the patient's tibia about the first fixation pin. The method also comprises advancing a second fixation pin into an anterior fixation pinhole of the tibial base trial component to prevent rotation of the tibial base trial component.

In some embodiments, positioning the tibial bearing trial component over the insert component may include advancing the tibial bearing trial component in a posterior direction into a gap defined between the tibial base trial component and the femoral trial component.

Additionally, in some embodiments, positioning the tibial bearing trial component over the insert component may further include securing the tibial bearing trial component to the insert component to prevent relative movement between the tibial bearing trial component and the tibial base trial component.

In some embodiments, securing the tibial bearing trial component to the insert component may include engaging the tibial bearing trial component with a posterior buttress of the insert component. The posterior buttress may include a post sized be received in an opening defined in the tibial bearing trial component and a pair of arms extending posteriorly from the post.

In some embodiments, securing the tibial bearing trial component to the insert component may further include engaging the tibial bearing trial component with an anterior buttress of the insert component.

Additionally, in some embodiments, advancing the first fixation pin into the posterior fixation pinhole may include positioning a head of the first fixation pin at or below a superior surface of the tibial bearing trial component, and positioning the tibial bearing trial component over the insert component may include engaging the tibial bearing trial component with the superior surface of the tibial bearing trial component.

In some embodiments, the method may also comprise selecting the insert component from a plurality of insert components. The plurality of insert components may include a first insert component configured to permit the tibial bearing trial component to rotate relative to the insert component and a second insert component configured to prevent the tibial bearing trial component from rotating relative to the insert component.

Additionally, in some embodiments, the method may also comprise inserting a keel punch into the patient's tibia after advancing the second fixation pin into the anterior fixation pinhole to define a surgically-prepared opening.

According to another aspect, a method of surgically preparing a patient's bone to receive a knee prosthesis comprises positioning a tibial base trial component on a surgically-prepared proximal end of a patient's tibia, positioning a femoral trial component on a surgically-prepared distal end of a patient's femur, inserting an insert component into an opening defined in the tibial base trial component, advancing a tibial bearing trial component in a posterior direction into a gap defined between the tibial base trial component and the femoral trial component, and securing the tibial bearing trial component to the insert component to prevent relative movement between the tibial bearing trial component and the tibial base trial component by engaging the tibial bearing trial component with a posterior buttress of the insert component that includes a post sized be received in an opening defined in the tibial bearing trial component and a pair of arms extending posteriorly from the post.

In some embodiments, securing the tibial bearing trial component to the insert component may further include engaging the tibial bearing trial component with an anterior buttress of the insert component. Additionally, inserting the insert component into the opening defined in the tibial base trial component may include inserting a keel of the insert component through the opening defined in the tibial base trial component and into the surgically-prepared proximal end of the patient's tibia.

In some embodiments, the method may include moving the patient's tibia between extension and flexion with the femoral trial component engaged with the tibial bearing trial component such that the tibial base trial component rotates on the proximal end of the patient's tibia. The method may further include advancing a fixation pin into a posterior fixation pinhole defined in the tibial base trial component. The tibial base trial component may rotate on the proximal end of the patient's tibia about the fixation pin as the patient's tibia is moved between extension and flexion.

In some embodiments, the method may include advancing a second fixation pin into an anterior fixation pinhole of the tibial base trial component to prevent rotation of the tibial base trial component.

Additionally, in some embodiments, the method may include removing the insert component from the tibial base trial component after advancing the second fixation pin into the anterior fixation pinhole, and inserting a keel punch into the patient's tibia to define a surgically-prepared opening.

In some embodiments, inserting the insert component into an opening defined in the tibial base trial component may include engaging a retention ring of the insert component with the tibial base trial component.

According to another aspect, a method of surgically preparing a patient's bone to receive a knee prosthesis comprises selecting a tibial bearing trial component, and selecting an insert component from a plurality of insert components. The plurality of insert components includes a first insert component configured to permit the tibial bearing trial component to rotate relative to the insert component and a second insert component configured to prevent the tibial bearing trial component from rotating relative to the insert component. The method further comprises positioning a tibial base trial component on a surgically-prepared proximal end of a patient's tibia and advancing the tibial bearing trial component in a posterior direction to position the tibial bearing trial component over the selected insert component. When the selected insert component is the first insert component, the method includes moving the patient's tibia between extension and flexion such that the tibial bearing trial component rotates on the tibial base trial component. When the selected insert component is the second insert component, the method includes advancing a first fixation pin into a posterior fixation pinhole defined in the tibial base trial component, and moving the patient's tibia between extension and flexion such that the tibial base trial component rotates on the proximal end of the patient's tibia about the first fixation pin.

BRIEF DESCRIPTION OF THE DRAWINGS

The detailed description particularly refers to the following figures, in which.

DETAILED DESCRIPTION OF THE DRAWINGS

Figure 1:
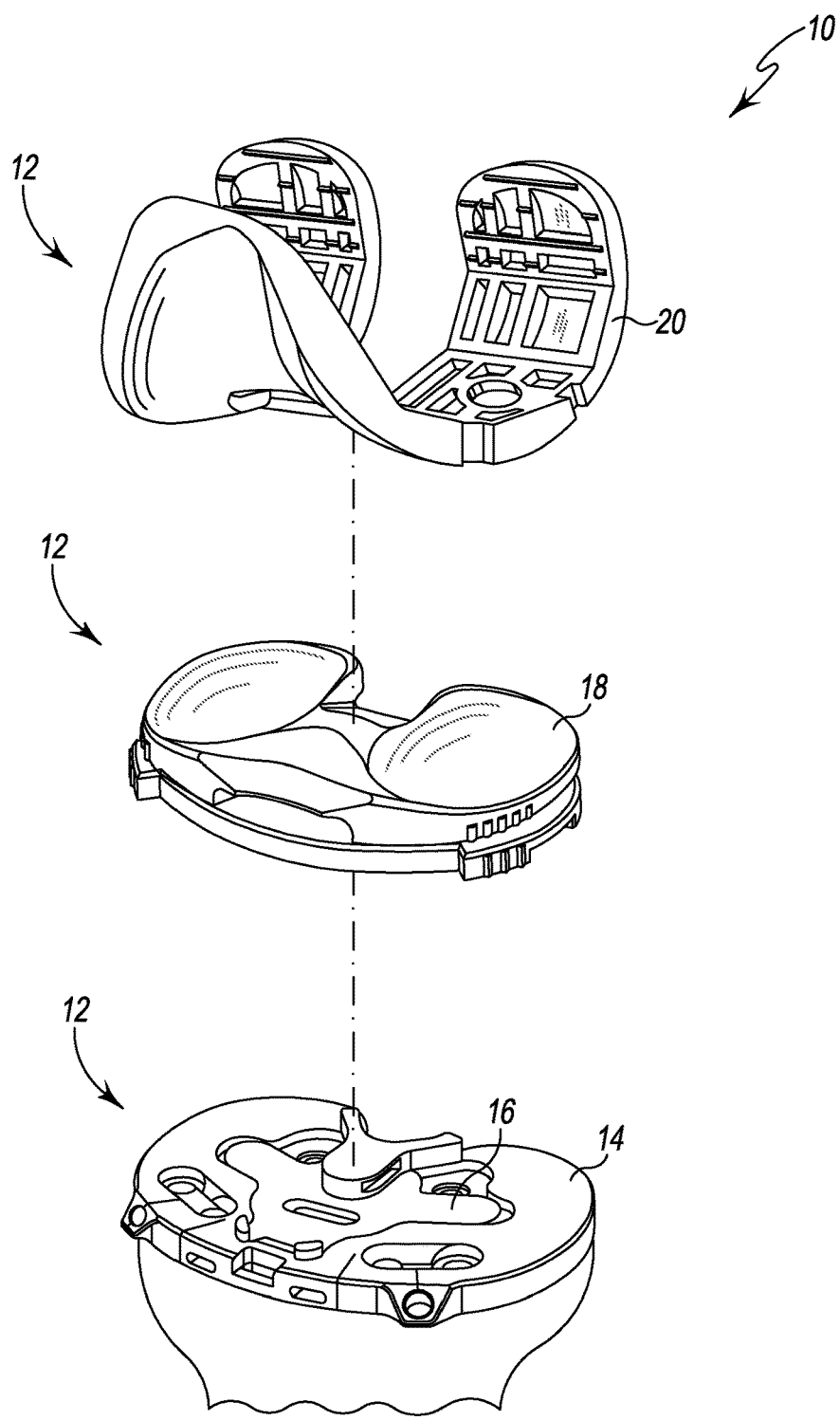
FIG. 1 is an exploded perspective view of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, et cetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-15, an orthopaedic surgical instrument system 10 (hereinafter system 10) is shown. The system 10 is used during joint arthroplasty procedures, such as a total knee replacement procedure. It should be appreciated, however, that although the system 10 is described below in regard to the performance of a total knee replacement procedure, certain concepts associated with the system 10 may be utilized in replacement procedures of numerous other joints throughout the body.

Figure 2:
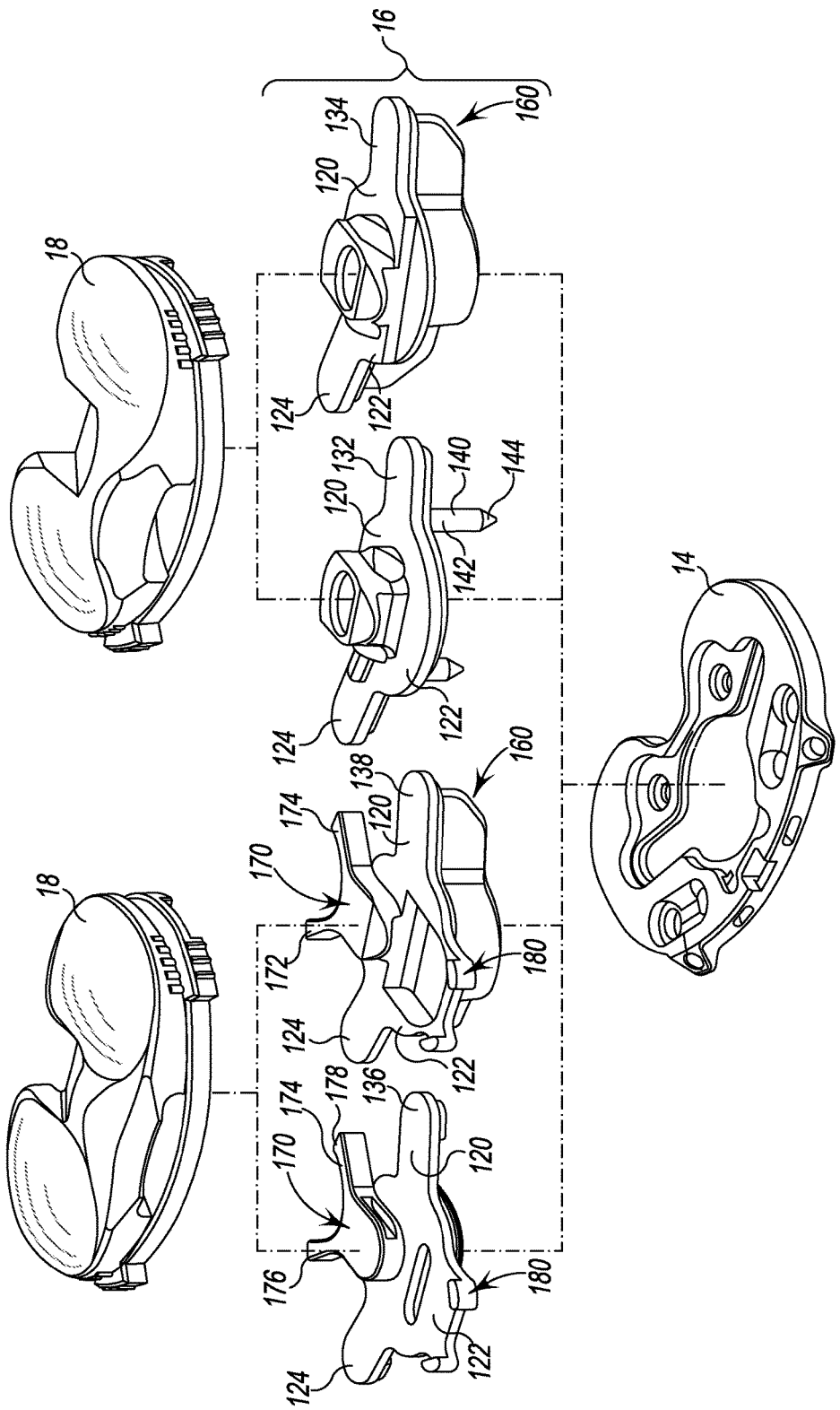
FIG. 2 is an exploded perspective view of a tibial base trial component, a number of tibial evaluation components, and a number of tibial bearing trial components of the orthopaedic surgical instrument system of FIG. 1.

As shown in FIGS. 1-2, the system 10 has a number of trial components 12, including a tibial base trial component 14, a number of insert components 16, a number of tibial bearing trial components 18, and a femoral trial component 20. In the illustrative embodiment, the system 10 also includes a number of fixation pins 250, a tibial keel punch 374, and a number of other surgical tools, such as, for example, an alignment handle (not shown), an impaction handle 372, and a fixation pin extraction tool 300, which are used to manipulate the trial components 12, the fixation pins 250, and the other surgical instruments during the performance of an orthopaedic surgical procedure, as described in greater detail below.

The system 10 may be utilized to size and select the prosthetic components of a knee prosthesis that will replace the patient's natural joint. To do so, the femoral trial component 20 is attached to a surgically-prepared distal end 406 of a patient's femur 404 (see FIGS. 18-20), whereas the tibial base trial component 14 is attached to a surgically-prepared proximal end 402 of a patient's tibia 400 (see FIGS. 18-20). As shown in FIG. 1, one of the insert components 16 may be positioned in the tibial base trial component 14. Further, one of the tibial bearing trial components 18 may be positioned between the femoral trial component 20 and the tibial base trial component 14. As described in greater detail below, the surgeon uses the system 10 during a surgical procedure in, for example, a trial reduction process, to determine the type and configuration of each of the various types of prosthetic components that are to be implanted and to surgically prepare the proximal end 402 of a patient's tibia 400 for implantation of a tibial prosthetic component.

Referring to FIG. 2, a number of tibial bearing trial components 18 of the system 10 are shown. In the illustrative embodiment, each tibial bearing trial component 18 is a multi-piece assembly that is configured to assist the surgeon in selecting a size and configuration of a prosthetic tibial bearing component of the knee prosthesis, as described in greater detail below. In other embodiments, each tibial bearing trial component 18 may be a unitary solid piece. The tibial bearing trial components 18 may include fixed tibial bearing trial components or mobile tibial bearing trial components of different sizes for different patients. An exemplary fixed tibial bearing trial component is shown on the left in FIG. 2. The term "fixed tibial bearing trial component" as used herein refers to the tibial bearing trial component 18 that is fixed in position relative to the tibial base trial component 14 when it is attached to a tibial base trial component 14. In other words, a fixed tibial bearing trial component is configured to not substantially rotate or move in the anterior-posterior direction or medial-lateral direction relative to the tibial base trial component 14. Such a fixed bearing trial component 18 may be embodied as a cruciate retaining trial, a posterior stabilized trial, a revision trial, or other surface trial configuration, per the surgeon's preference.

An exemplary mobile tibial bearing trial component is shown on the right in FIG. 2. The term "mobile tibial bearing trial component" as used herein refers to a tibial bearing trial component 18 that is permitted to rotate relative to the tibial base trial component 14 when it is attached a tibial base trial component 14. In other words, a mobile tibial bearing trial component is configured to substantially rotate or move in the anterior-posterior direction or the medial-lateral direction relative to the tibial base trial component 14. The mobile bearing trial component 18 may be embodied as a cruciate retaining trial, a posterior stabilized trial, a revision trial, or other surface trial configuration, per the surgeon's preference.

Figure 3:
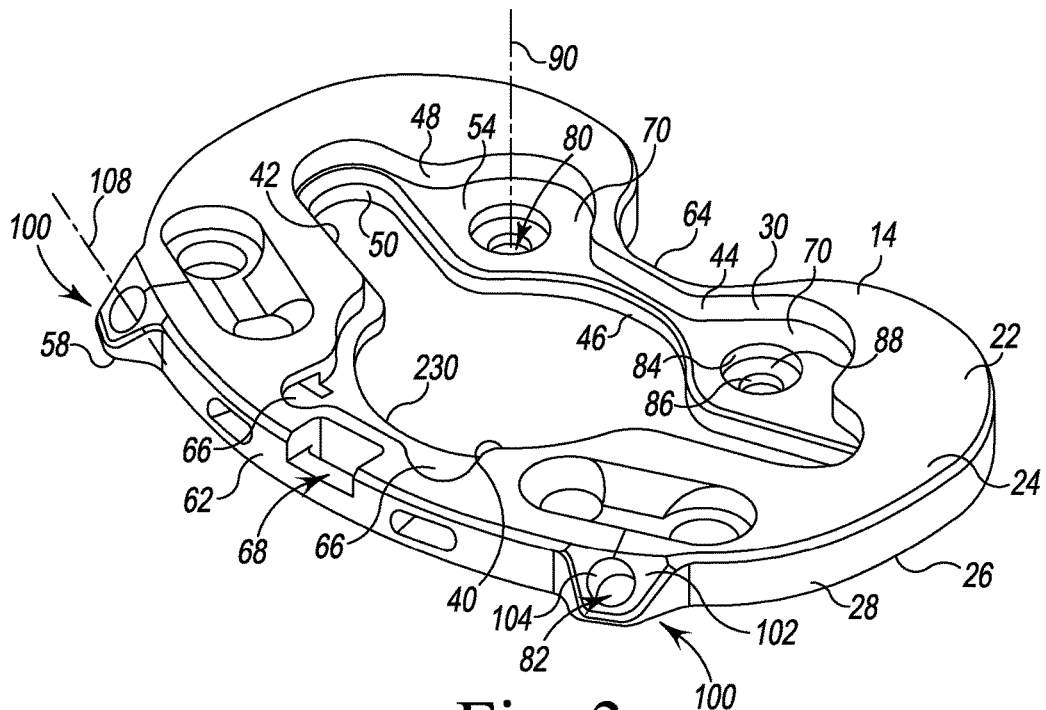
FIG. 3 is a perspective view of a tibial base trial component of the orthopaedic surgical instrument system of FIGS. 1 and 2.
Figure 4:
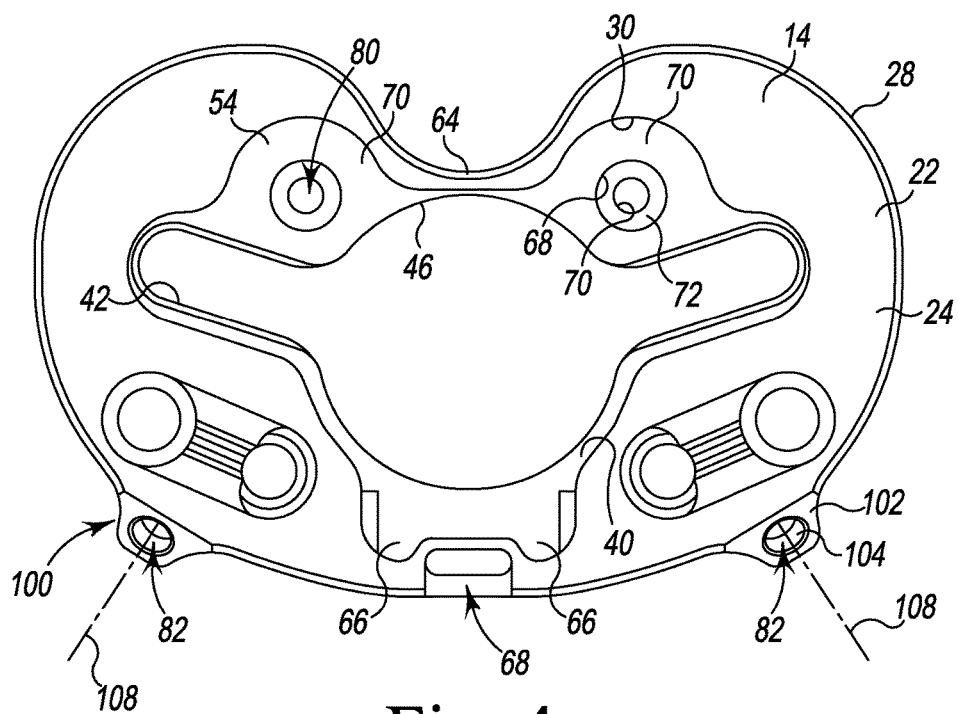
FIG. 4 is a top plan view of the tibial base trial component of FIG. 3.
Figure 5:
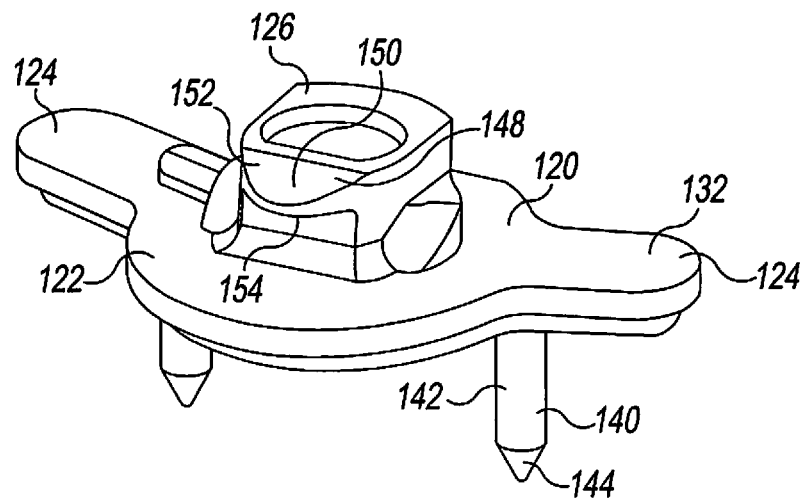
FIG. 5 is a perspective view of one of the tibial evaluation components of FIG. 2.

Regardless of the type of the tibial bearing trial component 18, the same tibial base trial component 14 may be attached to the surgically-prepared proximal end 402 of a patient's tibia 400. It should be appreciated that the tibial base trial component 14, like the other trial components 18, 20, may be formed in a number of different sizes to accommodate bones of various sizes. As shown in FIGS. 3-4, the tibial base trial component 14 includes a plate 22 having a superior surface 24, an inferior surface 26, and an outer sidewall 28 extending between the surfaces 24, 26. The plate 22 includes a plate opening 30 defined in the superior surface 24. The plate opening 30 has a central opening 40 and a pair of elongated openings 42 extending laterally and outwardly from the central opening 40. An inner wall 44 extends downwardly from the plate opening 30 to define a passageway 46 through the plate 22. The inner wall 44 includes an upper wall 48 and a lower wall 50 that is offset or otherwise spaced inwardly from the upper wall 48. The upper wall 48 and the lower wall 50 cooperate to define a shelf surface 54 positioned between the inferior surface 26 and the superior surface 24. As will be discussed in greater detail below, the configuration of the passageway 46 permits the advancement of various surgical drills, punches, and other instruments into the proximal end 402 of the patient's tibia 400.

The upper wall 48 of the plate 22 defines a number of slots 60 that are positioned in an anterior aspect 62 and a posterior aspect 64 of the plate 22. As shown in FIGS. 3-4, the slots 60 include a pair of anterior slots 66 that are positioned on each side of a lever-receiving notch 68 defined in the outer sidewall 28 of the plate 22. A pair of posterior slots 70 are positioned adjacent to each of the elongated openings 42. In the illustrative embodiment, all slots 60 extend downwardly from the plate opening 30 to the shelf surface 54.

As shown in FIGS. 3-4, the plate 22 of the tibial base trial component 14 further includes a pair of posterior fixation pinholes 80 and a pair of anterior fixation pinholes 82 that receive corresponding fixation pins 250 to secure the tibial base trial component 14 to the patient's tibia 400. The posterior fixation pinholes 80 have the same shape as the anterior fixation pinholes 82 but are uniquely sized. In the illustrative embodiment, each posterior fixation pinhole 80 has a matching diameter, but each anterior fixation pinhole 82 has a diameter that is greater than the diameters of the posterior fixation pinholes 80 to prevent the surgeon from inserting the wrong fixation pin 250, as described in greater detail below. It should be appreciated that in other embodiments the fixation pinholes 80, 82 may have rectangular, square, triangular, or other geometric shape. Additionally, although the fixation pinholes 80, 82 have the same shape in the illustrative embodiment, it should be appreciated that in other embodiments each opening may have a unique shape.

In the illustrative embodiment, the pair of posterior fixation pinholes 80 is defined in the posterior aspect 64 of the tibial base trial component 14 in a section of the shelf surface 54. Each posterior fixation pinhole 80 extends downwardly from an opening defined in the shelf surface 54 through the inferior surface 26 of the plate 22 to permit a fixation pin to advance into a patient's bone. In the illustrative embodiment, each posterior fixation pinhole 80 includes a pinhole upper wall 84 and a pinhole lower wall 86. The pinhole upper wall 84 extends downwardly from the shelf surface 54 to a pinhole shelf surface 88. The pinhole lower wall 86 extends downwardly from the pinhole shelf surface 88 to the inferior surface 26 of the plate 22 of the tibial base trial component 14. As shown in FIGS. 3-4, each posterior fixation pinhole 80 has a longitudinal axis 90 extending perpendicular to the superior surface 24.

The pair of anterior fixation pinholes 82 are defined in a pair of anterior tabs 100 extending anteriorly from the plate 22 of the tibial base trial component 14. As shown in FIGS. 3-4, one tab 100 is positioned on each side of the lever-receiving notch 68. Each anterior tab 100 has a superior inclined surface 102 that is angled relative to the substantially planar superior surface 24 and substantially planar inferior surface 26. Each anterior fixation pinhole 82 is defined in the center of the inclined surface 102 by an inner sidewall 104 that extends downwardly from the inclined surface 102 of each anterior tab 100 to an inferior surface 106. Each anterior fixation pinhole 82 has a longitudinal axis 108 that extends perpendicular to the inclined surface 102 and at an angle relative to the axes 90 of the posterior fixation pinholes 80. As shown in FIG. 4, the axes 108 of each anterior fixation pinhole 82 are angled relative to each other. In that way, a fixation pin positioned in either anterior fixation pinhole 82 is engaged with the proximal end 402 of the patient's tibia 400 at an oblique angle, as will be described in detail below.

Returning to FIG. 2, the system 10 includes a number of insert components 16 of the system 10, which are selected according based on the type of the tibial bearing trial component 18 selected for a particular patient. Specific exemplary insert components 16 are shown and described in detail in FIGS. 5-11, as will be described in greater detail below. Generally, the insert component 16 is embodied as a tibial evaluation component or "evaluation bullet." Each tibial evaluation component 16 is configured to be positioned separately in the plate opening 30 of the tibial base trial component 14. Each tibial evaluation component 16 has a base plate 120 having a central platform 122 and a pair of prongs 124 that extend outwardly from the central platform 122. A post 126 extends upwardly from the central platform 122 of each tibial evaluation component 16.

As shown in FIG. 2, the tibial evaluation components 16 include a pair of mobile bearing evaluation components 132, 134, which may be used with the mobile tibial bearing trial component, and a pair of the fixed bearing evaluation components 136, 138, which may be used with the fixed tibial bearing trial component. As shown in detail in FIG. 5, the mobile bearing evaluation component 132 includes a pair of mounting spikes 140 that extend downwardly from the prongs 124. Each spike 140 includes an upper cylindrical section 142 and a pointed conical tip 144 configured to engage the proximal end 402 of the patient's tibia 400, thereby temporarily securing the tibial evaluation component 132 and the tibial base trial component 14 to the proximal end 402 of the patient's tibia 400. In that way, the assembly formed by the components 14, 132 may be prevented from moving relative to the patient's tibia. The post 126 of the mobile bearing evaluation component 132 includes a connector 148 that is formed in its superior end. The connector 148 is configured to receive a locking flange associated with an impaction handle 372 so as to secure the tibial evaluation component 16 to the impaction handle 372. The connector 148 includes a flange 150 that extends anteriorly away from the longitudinal axis of the post 126. The flange 150 has a ramp surface 152 defined therein. In particular, an inferior surface 154 of the flange 150 extends substantially parallel to a superior surface 156 of the tibial evaluation component's base plate 120, whereas the flange's superior surface 158 inclines superiorly in the anterior-to-posterior direction. The ramp surface 152 facilitates installation of the tibial bearing trial assembly and is further described in co-pending U.S. patent application Ser. No. 14/265,960, entitled "TIBIAL TRIAL SYSTEM FOR A KNEE PROSTHESIS" by David Waite et al. and filed on Apr. 30, 2014, which is incorporated herein by reference.

Figure 6:
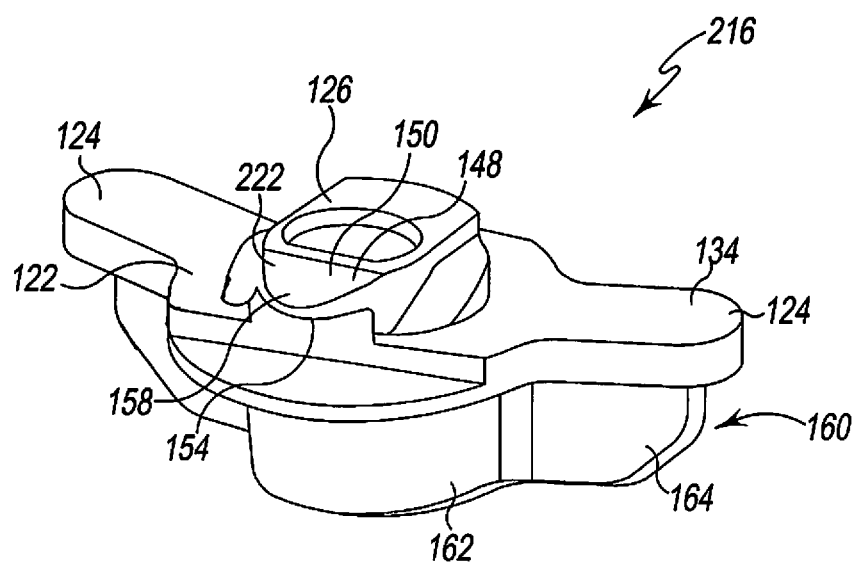
FIG. 6 is a perspective view of another tibial evaluation component of FIG. 2.

Referring now to FIG. 6, another mobile evaluation component 134 is shown. The evaluation component 134 shares many common features with the tibial evaluation component 132, and the same reference numbers will be used to describe those common features. Additionally, the component 134, like the other evaluation components 16, includes a base plate 120 having a central platform 122 and a pair of prongs 124 that extend outwardly from the central platform 122. A post 126 extends upwardly from the central platform 122 of each tibial evaluation component 16 and, like the other mobile evaluation component 132, also includes a connector 148 that is formed in its superior end. The connector 148 is configured to receive a locking flange associated with the impaction handle 372. The connector 148 includes a flange 150 that extends anteriorly away from the longitudinal axis of the post 126. The flange 150 has a ramp surface 152 defined therein. In particular, an inferior surface 154 of the flange 150 extends substantially parallel to a superior surface 156 of the tibial evaluation component's base plate 120, whereas the flange's superior surface 158 inclines superiorly in the anterior-to-posterior direction.

The mobile evaluation component 134 also includes a sleeve 160 that extends downwardly from the central platform 122 and the prongs 124. The sleeve 160 includes a central stem 162 sized to be received in the central opening 40 of the tibial base trial component 14. The sleeve 160 further includes a pair of prongs 164 that extend outwardly from the central stem 162, which are sized to be received in the elongated openings 42 of the tibial base trial component 14. As described in greater detail below, the sleeve 160 is sized to extend through the tibial base trial component 14 and into a surgically-prepared opening in the patient's tibia and thereby prevent the components 14, 134 from rotating on the patient's tibia.

Returning to FIG. 2, the tibial evaluation components 16 also include the pair of fixed bearing elevation components 136, 138. Each of the evaluation components 136, 138 has a base plate 120 having a central platform 122 and a pair of prongs 124 that extend outwardly from the central platform 122. A post 126 extends upwardly from the central platform 122 of each tibial evaluation component 16. In the illustrative embodiment, the post 126 of each of the evaluation components 136, 138 is included in a posterior buttress 170. In addition to the post 126, each posterior buttress 170 includes a pair of arms 172, 174 that extend posteriorly from the post 126 to cantilevered tips 176, 178. Each of the evaluation components 136, 138 also includes an anterior buttress 180. As described in greater detail below, the buttresses 170, 180 cooperate to prevent rotation and movement of the fixed bearing trial component 18 relative to the tibial base trial component 14.

Figure 7:
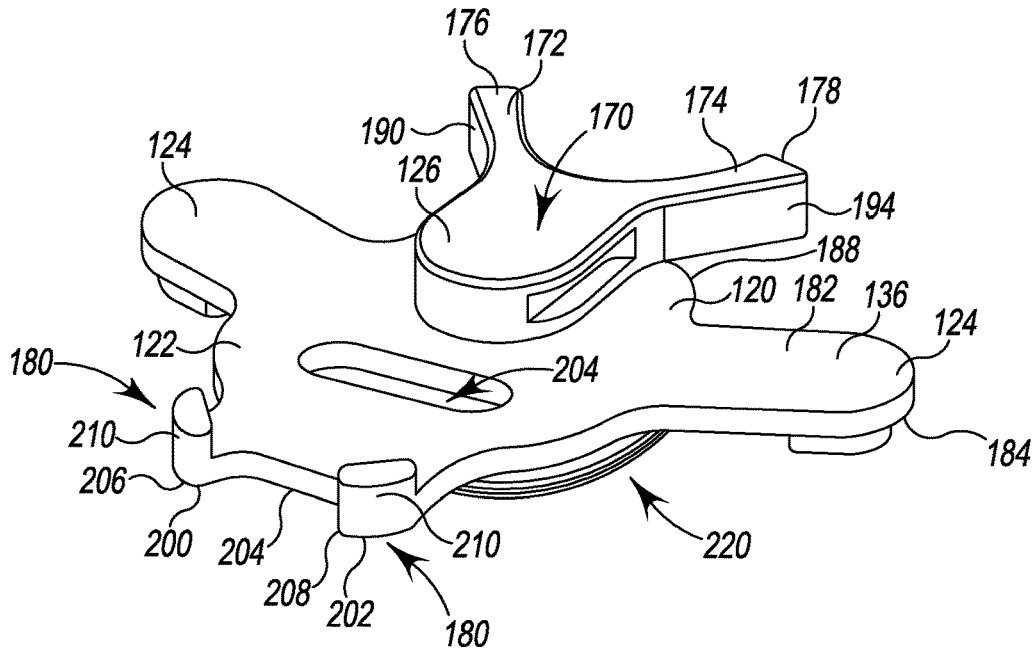
FIG. 7 is a perspective view of another tibial evaluation component of FIG. 2.
Figure 8:
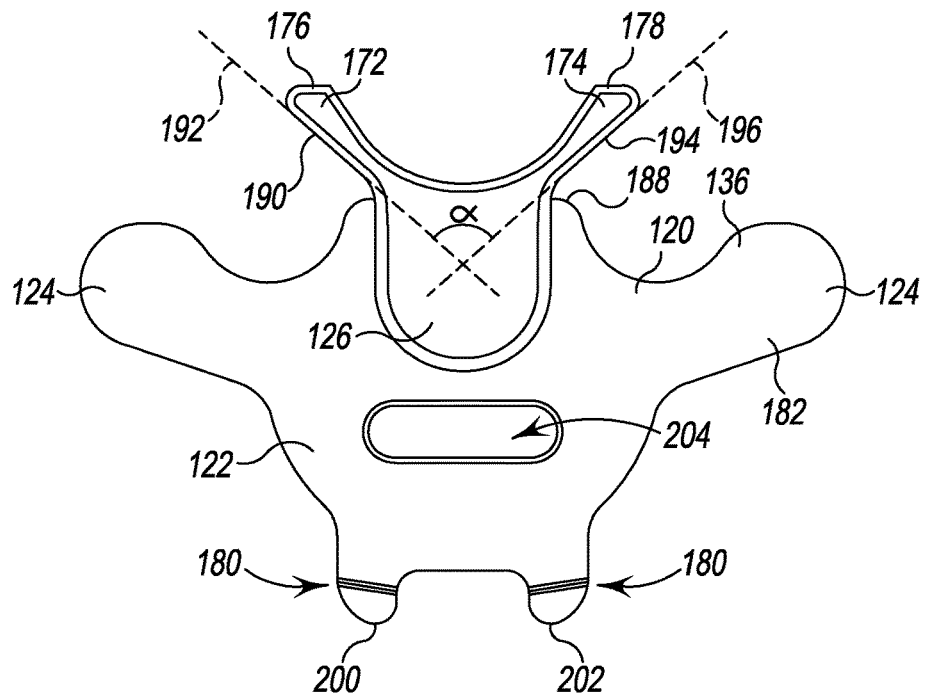
FIG. 8 is a top plan view of the tibial evaluation component of FIG. 7.
Figure 9:
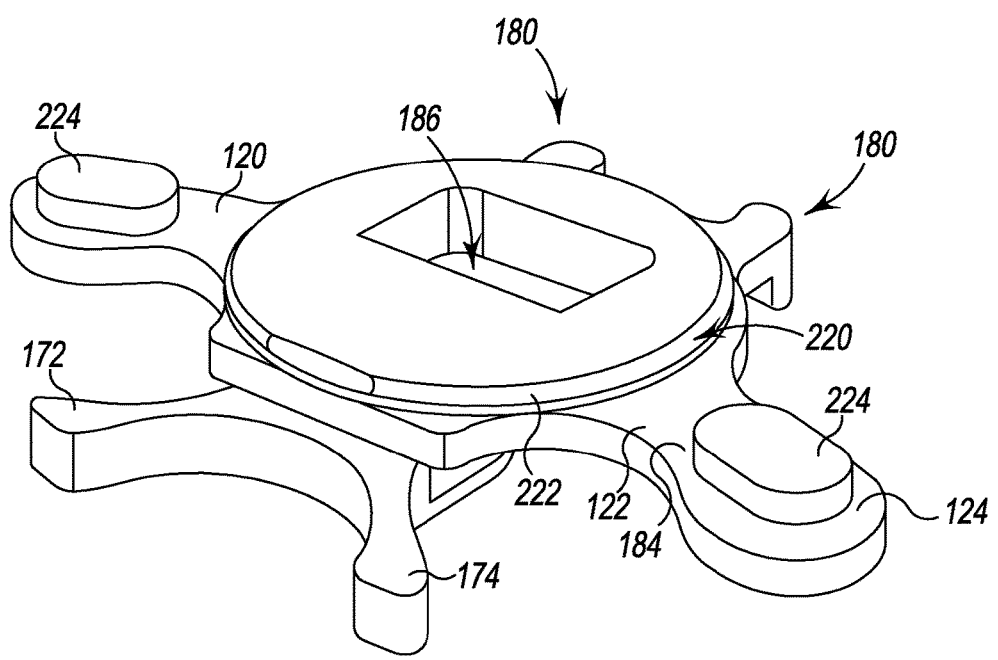
FIG. 9 is a bottom view of the tibial evaluation component of FIG. 7.

Referring now to FIGS. 7-9, the fixed evaluation component 136 is illustratively spikeless. As a result, when the fixed evaluation component 136 is attached to the tibial base trial component 14 on a patient's tibia, the assembly is permitted move relative to the patient's tibia unless restrained by a fixation pin 250. As described above, the evaluation component 136 includes a base plate 120 that has a superior surface 182 and an inferior surface 184 positioned opposite the superior surface. An aperture 186 extends through the surfaces 182, 184 in the central platform 122 of the base plate 120. In the illustrative embodiment, the aperture 186 is sized to receive a tip (not shown) of a removal tool to detach the evaluation component 136 from the tibial base trial component 14.

As described above, the evaluation component 136 also has a posterior buttress 170 that includes a post 126 and a pair of arms 172, 174 extending posteriorly from the post 126 to cantilevered tips 176, 178, respectively. As shown in FIG. 7, the post 126 is positioned on the posterior edge 188 of the base plate 120. The arm 172 defines a lateral-most sidewall 190 of the posterior buttress 170, which extends along a straight imaginary line 192. The other arm 174 defines a medial-most sidewall 194 of the posterior buttress 170, which extends along another straight imaginary line 196. As shown in FIG. 8, the pair of arms 172, 174 are positioned such that the imaginary line 192 intersects the other imaginary line 196 to define an angle α. In the illustrative embodiment, the angle α may have a magnitude of between 45 and 145 degrees, thereby giving the posterior buttress 170 a generally Y-shape.

As described above, the evaluation component 136 also includes an anterior buttress 180. As shown in FIGS. 7-8, the anterior buttress 180 includes a pair of arms 200, 202, which extend anteriorly from the anterior edge 204 of the base plate 120 to cantilevered end 206, 208, respectively. Each arm 200, 202 has a tab 210 that extends superiorly from the respective ends 206, 208 of the arms 200, 202. In the illustrative embodiment, the tabs 210, post 126, and arms 172, 174 cooperate to define a retention mechanism that engages a fixed bearing trial component 18 and prevents rotation and movement of the fixed bearing trial component 18 relative to the tibial base trial component 14.

Referring now to FIG. 9, the base plate 120 of the tibial evaluation component 126 further includes an attachment mechanism 220 to secure the evaluation component 126 to the tibial base trial component 14. In the illustrative embodiment, the attachment mechanism 220 includes a retention ring 222 and a pair of blocks 224 extending downwardly from the base plate 120. The retention ring 222 extends from the inferior surface 184 of the central platform 122, and each of the blocks 224 is positioned on the inferior surface 184 of each prong 124. When the tibial evaluation component 136 is seated on the tibial base trial component 14, the central platform 122 of the tibial evaluation component 126 is received in the central opening 40 of the tibial base trial component 14, and the prongs 124 are received in the elongated openings 42 of the tibial base trial component 14.

As shown in FIG. 3, the tibial base trial component 14 includes an annular flange 230 that extends around the central opening 40. When the tibial evaluation component 136 is seated on the tibial base trial component 14, the retention ring 222 of the evaluation component 126 extends through the central opening 40 of the tibial base trial component 14 and engages the annular flange 230, thereby securing the components 14, 136 together. Further, the pair of blocks 224 extend into the elongated openings 42 of the tibial base trial component 14. The retention ring 222 and blocks 224 are sized to not extend beyond the inferior surface 26 of the tibial base trial component 14 such that when the fixed evaluation component 136 is attached to the tibial base trial component 14 on a patient's tibia 400, the assembly is permitted to move relative to the patient's tibia 400 unless restrained by a fixation pin 250.

Figure 10:
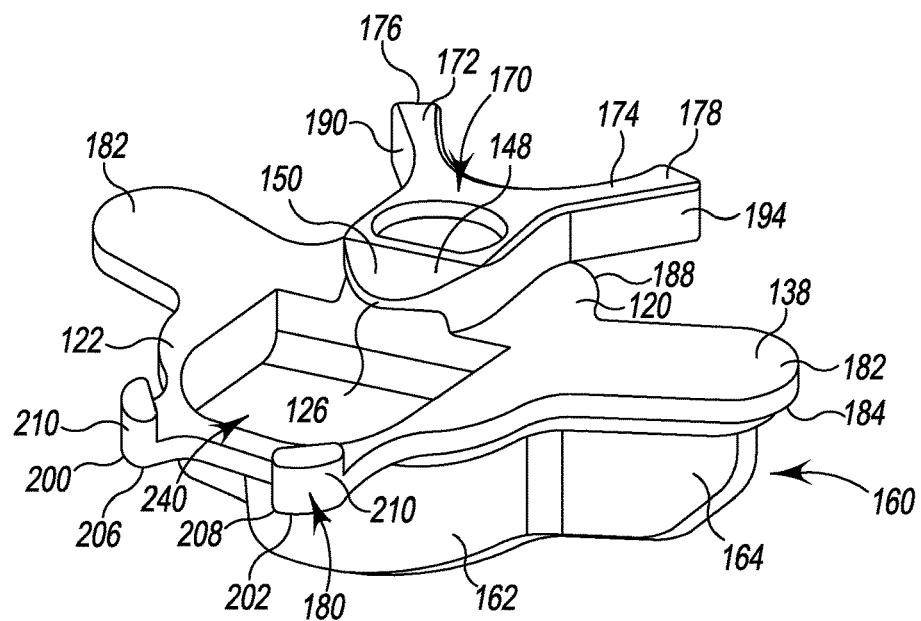
FIG. 10 is a perspective view of another tibial evaluation component of FIG. 2.
Figure 11:
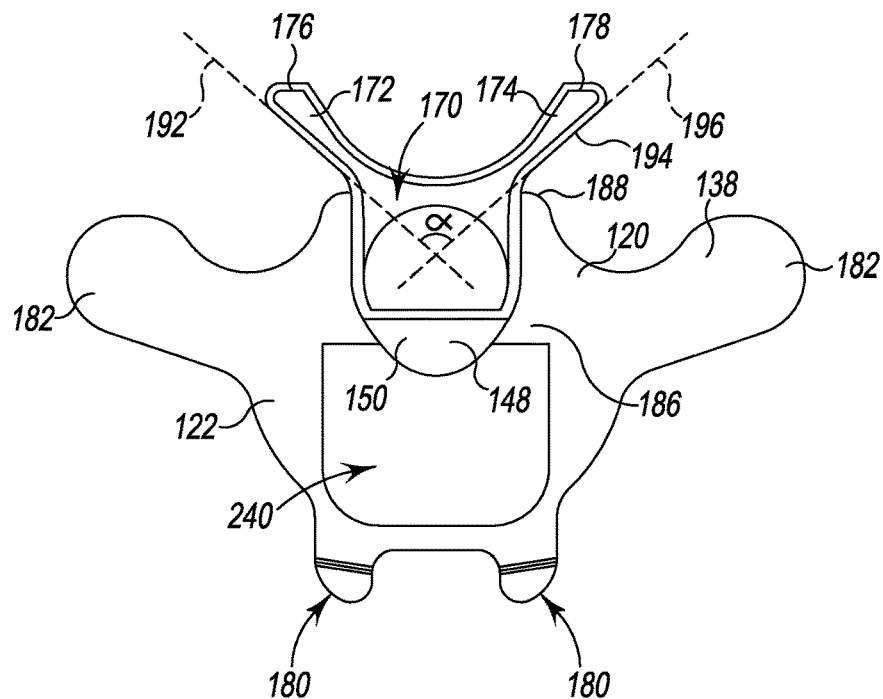
FIG. 11 is a top plan view of the tibial evaluation component of FIG. 10.

As described above, the instrument system 10 also includes another fixed evaluation component 138, which is shown in FIGS. 10-11. The evaluation component 138 shares many common features with the other evaluation components 132, 134, 136, and the same reference numbers will be used to describe those common features. As described above, the evaluation component 138 includes a base plate 120 that has a superior surface 182 and an inferior surface 184 positioned opposite the superior surface. An closed aperture 240 is defined in the superior surface 182 of the central platform 122 of the base plate 120. In the illustrative embodiment, the aperture 240 is sized to receive a tip of a removal tool, such as, for example, impaction handle 372, to detach the evaluation component 138 from the tibial base trial component 14.

As described above, the evaluation component 136 also has a posterior buttress 170 that includes a post 126 and a pair of arms 172, 174 extending posteriorly from the post 126 to cantilevered tips 176, 178, respectively. As shown in FIG. 10, the post 126 is positioned on the posterior edge 188 of the base plate 120. The arm 172 defines a lateral-most sidewall 190 of the posterior buttress 170, which extends along a straight imaginary line 192. The other arm 174 defines a medial-most sidewall 194 of the posterior buttress 170, which extends along another straight imaginary line 196. As shown in FIG. 11, the pair of arms 172, 174 are positioned such that the imaginary line 192 intersects the other imaginary line 196 to define an angle α. In the illustrative embodiment, the angle α may have a magnitude of between 45 and 145 degrees, thereby giving the posterior buttress 170 a generally Y-shape.

As described above, the evaluation component 138 also includes an anterior buttress 180. As shown in FIGS. 10-11, the anterior buttress 180 includes a pair of arms 200, 202, which extend anteriorly from the anterior edge 204 of the base plate 120 to cantilevered end 206, 208, respectively. Each arm 200, 202 has a tab 210 that extends superiorly from the respective ends 206, 208 of the arms 200, 202. In the illustrative embodiment, the tabs 210, post 126, and arms 172, 174 cooperate to define a retention mechanism that engages a fixed bearing trial component 18 and prevents rotation and movement of the fixed bearing trial component 18 relative to the tibial base trial component 14.

Like the mobile evaluation components 132, 134, the evaluation component 138 also includes a connector 148 that is formed at the superior end of the post 126. The connector 148 is configured to receive a locking flange associated with the impaction handle 372. In the illustrative embodiment, the connector 148 includes a flange 150 that extends anteriorly away from the longitudinal axis of the post 126. As shown in FIGS. 10-11, the flange 150 is positioned above the closed aperture 240.

The fixed evaluation component 138 also includes a sleeve 160 that extends downwardly from its central platform 122 and prongs 124. The sleeve 160 includes a central stem 162 sized to be received in the central opening 40 of the tibial base trial component 14. The sleeve 160 further includes a pair of prongs 164 that extend outwardly from the central stem 162, which are sized to be received in the elongated openings 42 of the tibial base trial component 14. As described in greater detail below, the sleeve 160 is sized to extend through the tibial base trial component 14 and into a surgically-prepared opening in the patient's tibia and thereby prevent the components 14, 138 from rotating on the patient's tibia.

Figure 12:
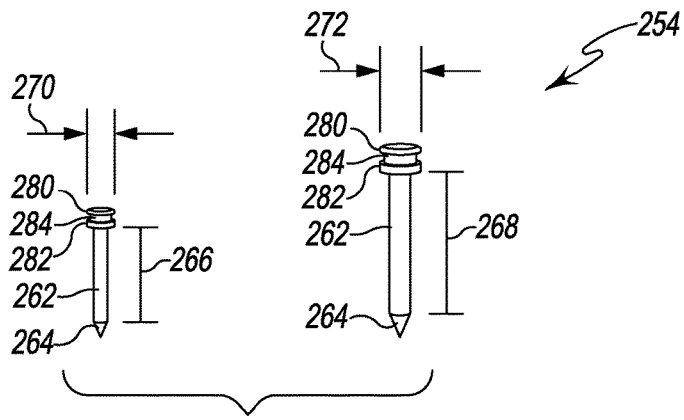
FIG. 12 is a perspective view of a posterior fixation pin and an anterior fixation pin.

As described above, the surgical instrument system 10 also includes a number of fixation pins 250 for use with the tibial base trial component 14. As shown in FIG. 12, the fixation pins 250 include a posterior fixation pin 252 that is sized to be received in either of the posterior fixation pinholes 80 of the tibial base trial component 14 and an anterior fixation pin 254 that is sized to be received in either of the anterior fixation pinholes 82. Each of the fixation pins 252, 254 includes a pin head 260 and a cylindrical shaft 262 that extends from the pin head 260 to a pointed conical tip 264 that is configured to engage the proximal end 402 of the patient's tibia 400. The shaft 262 of the pin 252 defines a length 266 that is shorter than a corresponding length 268 defined by the shaft 262 of the pin 254. Additionally, in the illustrative embodiment, the shaft 262 of the pin 252 has a diameter 270 that is smaller than a corresponding diameter 272 of the shaft 262 of the other pin 254.

As shown in FIG. 12, the pin head 260 of each of the pins 252, 254 has a similar configuration. The pin head 260 includes an outer ring 280 and an inner ring 282 that is spaced apart from the outer ring 280. A groove 284 is defined between the rings 280, 282. The rings 280, 282 have the same diameter in size, which is greater than the diameters 270, 272 of either of the pins 252, 254. As described in greater detail below, the surgeon positions a portion of a pin extraction tool 300 into the groove 284 to manipulate the pins 252, 254.

Figure 13:
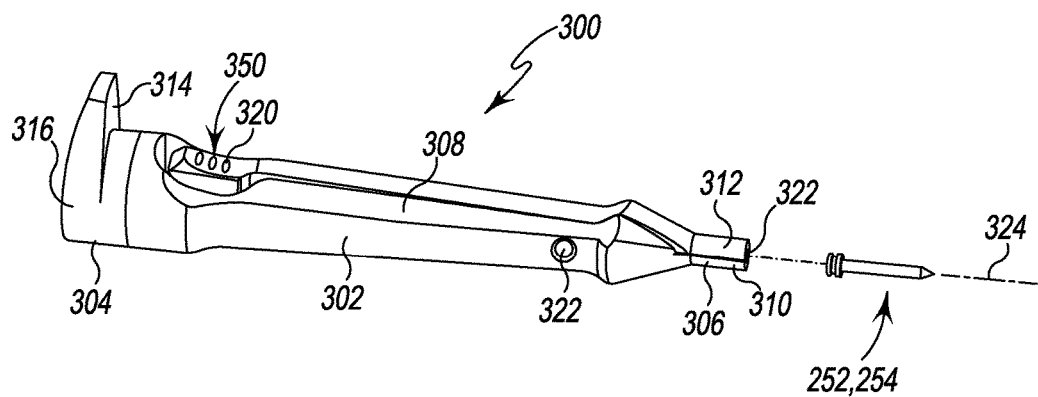
FIG. 13 is a perspective view of one of the fixation pin and a pin extraction tool of the orthopaedic surgical instrument system of FIG. 1.

As shown in FIG. 13, the pin extraction tool 300 includes an elongated body 302 that extends from a proximal end 304 to a distal end 306. The extraction tool 300 also includes a lever arm 308 that is pivotally coupled to the elongated body 302. A pair of opposing jaws 310, 312 are defined on the distal ends of the elongated body 302 and lever arm 308, respectively. As described in greater detail below, the jaws 310, 312 are configured to engage the pin heads 260 of the fixation pins 252, 254.

The elongated body 302 includes an impaction plate 314 that is positioned at the proximal end 304 and a grip 316 sized to receive a hand of a user. A longitudinal channel 318 is defined in the body 302, which is sized to receive the lever arm 308. The lever arm 308 includes a push button 320 that is positioned near the proximal end 304 of the body 302, and the lever arm 308 is coupled to the elongated body 302 via a locking pin 322. As shown in FIG. 13, the locking pin 322 defines an axis of rotation 324 about which the lever arm 308 pivots to move between an engaged position (FIG. 14) in which the jaws 310, 312 capture a pin head 260 of one of the fixation pins 252, 254 and a disengaged position (FIG. 15) in which the pin head 260 may be detached from the tool 300.

Figures 14, 15:
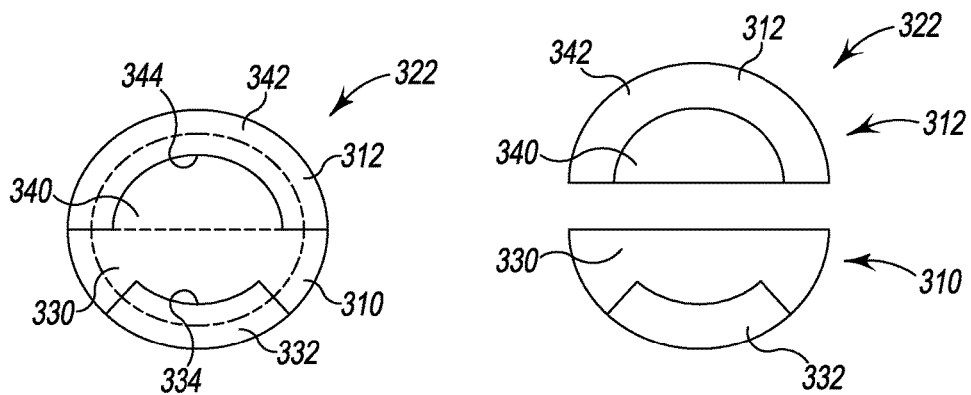
FIG. 14 is a front elevation view showing the pin extraction tool of FIG. 11 in a closed position.
FIG. 15 is a view similar to FIG. 12 showing the pin extraction tool in an open position.

As shown in FIG. 14, the lower jaw 310 includes a distal face 330 of the elongated body 302. The distal face 330 is semi-circular and has an annular flange or lip 332 extending outwardly therefrom. A groove 334 is defined between the face 330 and the lip 332, which is sized to receive the outer ring 280 of fixation pin 252 or fixation pin 254. In the illustrative embodiment, the lip 332 extends over only a portion of distal face 330. As shown in FIG. 14, the lip 332 defines an arc that is less than 180 degrees.

The upper jaw 312 includes a distal face 340 of the lever arm 308. The distal face 340 is semi-circular and has an annular flange or lip 342 extending outwardly therefrom. A groove 344 is defined between the face 340 and the lip 342, which is sized to receive the outer ring 280 of fixation pin 252 or fixation pin 254. In the illustrative embodiment, the lip 342 extends over the distal face 340 such that a pair of gaps 346, 348 is defined between the lips 332, 342. As shown in FIG. 14, the lip 342 is semi-circular.

In use, a user may depress the push button 320 in the direction indicated by arrow 350 in FIG. 13 to actuate the lever arm 308. The lever arm 308 may then pivot about the axis 324 to move the jaws 310, 312 apart, as shown in FIG. 15. In the disengaged position shown in FIG. 15, a surgeon may advance a pin head 260 between the jaws 310, 312 and move the outer ring 280 into engagement with the lower lip 332 of the lower jaw 310. When the surgeon releases the push button 320, a spring or other biasing member (not shown) causes the lever arm 308 to pivot back to the engaged position shown in FIG. 14, thereby advancing the upper lip 342 of the upper jaw 312 into engagement with the outer ring 280 of the pin head 260. In that way, the jaws 310, 312 cooperate to provide positive engagement with the pin head 260, and the fixation pin is retained in the extraction tool 300 and may be implanted or extracted from the patient's body.

Figure 16:
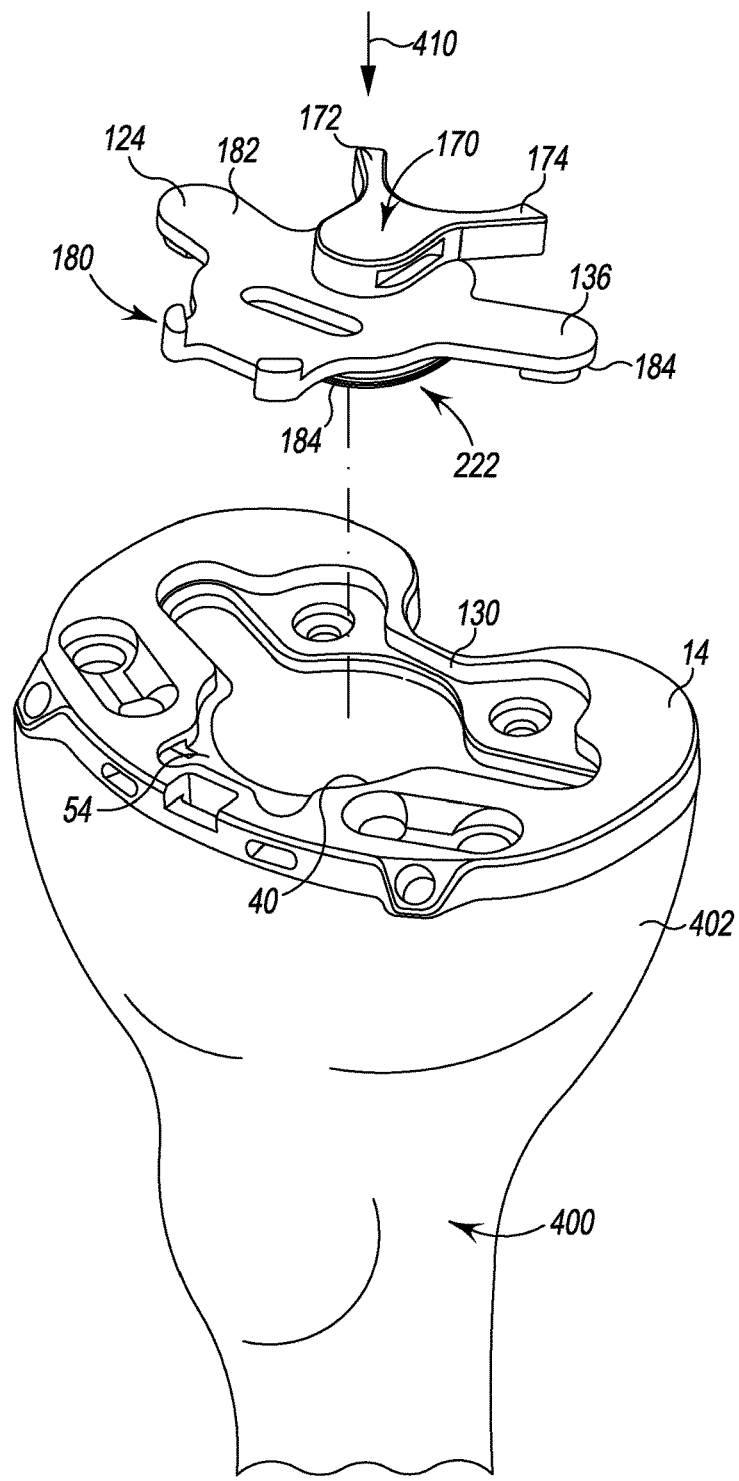
FIGS. 16-22 is views of a patient's femur, tibia, and the orthopaedic surgical instrument system of FIG. 1 as the orthopaedic surgical instrument system is used in the performance of a surgical procedure to implant a knee prosthesis.

Referring now to FIGS. 16-22, portions of an orthopaedic surgical procedure utilizing the system 10 are shown. The surgeon may first perform a resection of the distal end 406 of the patient's femur 404 and a resection of the proximal end 402 of the patient's tibia 400 to surgically prepare those ends for trial reduction and subsequent attachment of the knee prosthetic components. For example, as shown in FIG. 16, the surgically-prepared proximal end 402 of the patient's tibia 400 includes a resected surface configured to receive the tibial base trial component 14.

The surgeon may position the tibial base trial component 14 on the resected surface of the patient's tibia 400. The surgeon may then select one of the tibial evaluation components 16 to be placed in the central opening 40 of the tibial base trial component 14. If the surgeon desires the fixed bearing trial component 18, the surgeon may select the spikeless tibial evaluation component 136 and position it in the central opening 40 by hand so that the inferior surface 184 of the tibial evaluation component engages the shelf surface 54 of the tibial base trial component 14. If the surgeon desires a mobile bearing trial component 18, the surgeon may select the spiked tibial evaluation component 132. In some embodiments, the surgeon may use the spiked tibial evaluation component 132 for initial trial reduction before using the fixed tibial evaluation component 136. The use of mobile bearing trial component and the spiked tibial evaluation component is further described in co-pending U.S. patent application Ser. No. 14/265,960, entitled "TIBIAL TRIAL SYSTEM FOR A KNEE PROSTHESIS" by David Waite et al. and filed on Apr. 30, 2014.

Figure 17:
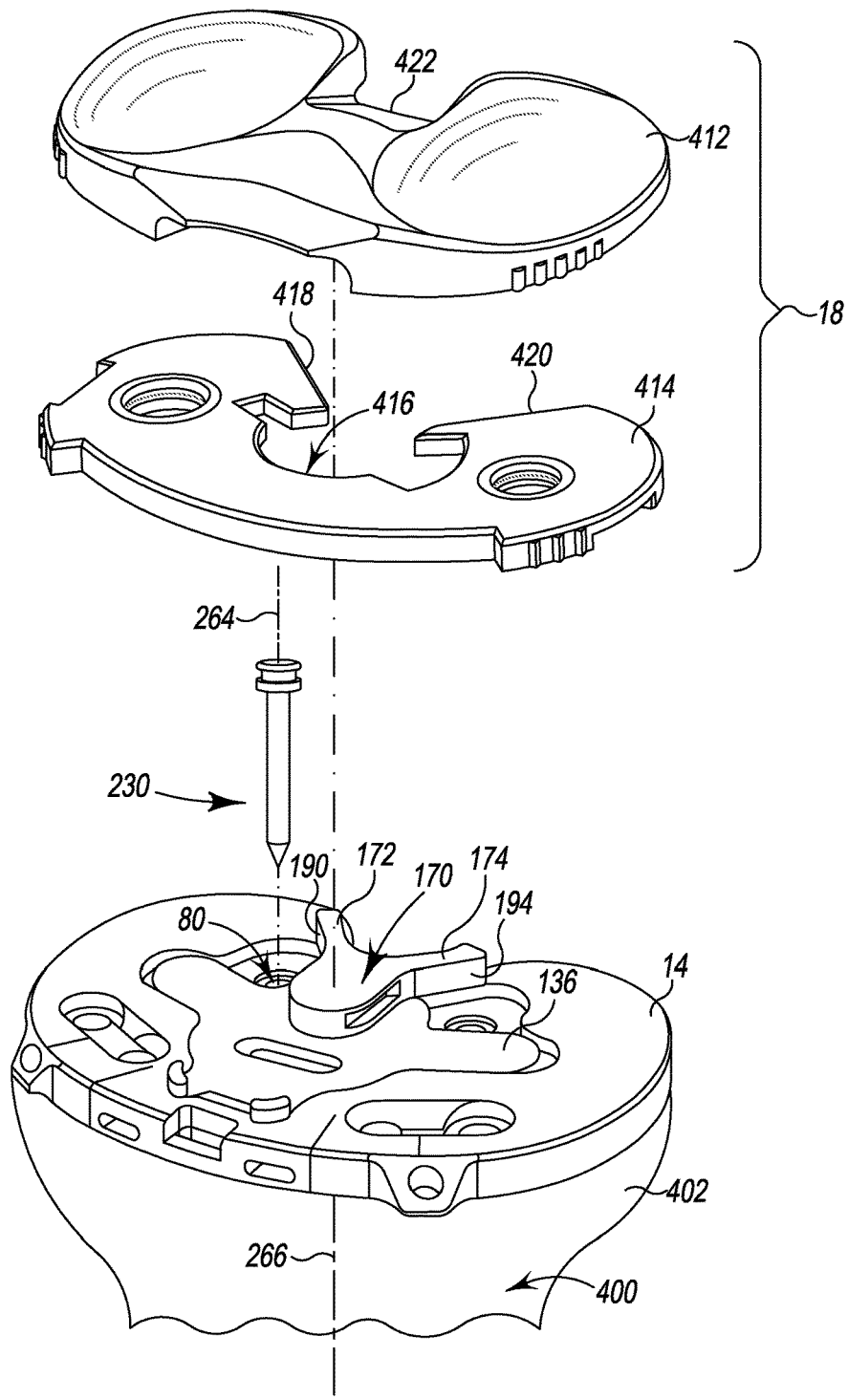

In the illustrative embodiment, the surgeon may grip the selected tibial evaluation component 136 by the posterior buttress 170 and position it over the plate opening 30 of the tibial base trial component 14. The surgeon may then apply force in the direction indicated by arrow 410 to the superior surface 182 of the evaluation component 136 to engage the inferior surface 184 of the tibial evaluation component 136 with the shelf surface 54 of the tibial base trial component 14, as shown in FIG. 17.

Once the tibial evaluation component 136 is properly received in the central opening 40 of the tibial base trial component 14, the surgeon may inferiorly advance a fixation pin 252 through one of the pinholes 80 of the tibial base trial component 14 into the proximal end 402 of the patient's tibia 400. When the posterior fixation pin 252 is properly inserted into the tibial base trial component 14, a longitudinal axis 264 of the posterior fixation pin 252 is perpendicular to the proximal surface of the patient's tibia 400 and is relatively parallel to a longitudinal axis 266 of the patient's tibia 400. The posterior fixation pin 252 temporarily anchors one end of the tibial base trial component 14 to the proximal end 402 of the patient's tibia 400. Inserting only one posterior fixation pin 252 in one of the posterior fixation pinhole 80 permits the tibial base trial component 14 to rotate about the fixation pin 252 while the surgeon performs the trial reduction.

Figure 22:
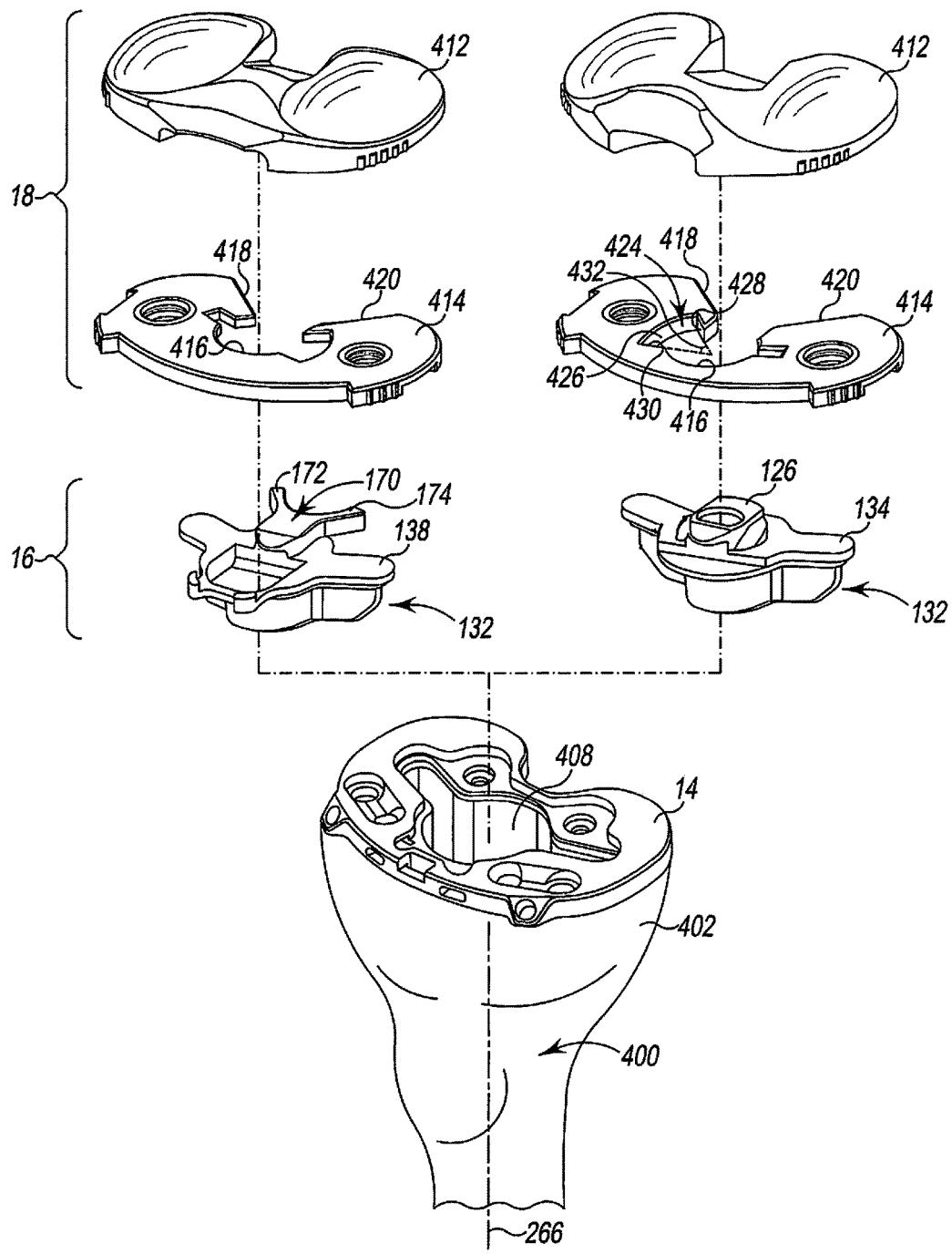

Once the posterior fixation pin 252 is properly inserted, the surgeon may assemble a fixed bearing trial component 18 or a mobile bearing trial component 18. The fixed bearing trial component 18 is shown in FIG. 17. As described above, the tibial bearing trial component 18 is a multi-piece assembly. Accordingly, a given tibial bearing trial component 18 may be assembled with one of a number of tibial bearing surface trial components 412 and one of a number of a plurality of trial shims 414, as shown in FIG. 22. In a single kit of trial components, the tibial bearing surface trial components 412 may be provided in different sizes and/or configurations, and each trial shim 414 may have a different thickness. Because each trial shim 414 is configured to be secured to each tibial bearing surface trial component 412, the surgeon is able to assemble a tibial bearing trial component 18 of one size and configuration, evaluate the performance of that tibial bearing trial component 18, and then modify the tibial bearing trial component 18 as necessary to determine intraoperatively the type and configuration of the prosthetic tibial bearing component to be implanted.

The surgeon may assemble one of the trial shim 414 with one of the tibial bearing surface trial components 412 to form a tibial bearing trial component 18. For example, the surgeon may select one of the fixed bearing surface trial components 412 and secure the trial shim 414 thereto to form a fixed bearing trial component 18. During a surgical trialing procedure, the fixed bearing trial component 18 is advanced such that the post 126 of the posterior buttress 170 of the tibial evaluation component 16 is received in a central passageway 416 of the trial shim 414. The trial shim 414 further includes two posterior sidewalls 418, 420 which are configured to cooperate with the anterior sidewalls 190, 194 of the arms 172, 174, respectively, of the posterior buttress 170 of the tibial evaluation component 136 to prevent the fixed tibial bearing trial component from rotating relative to the tibial base trial component 14.

Figure 18:
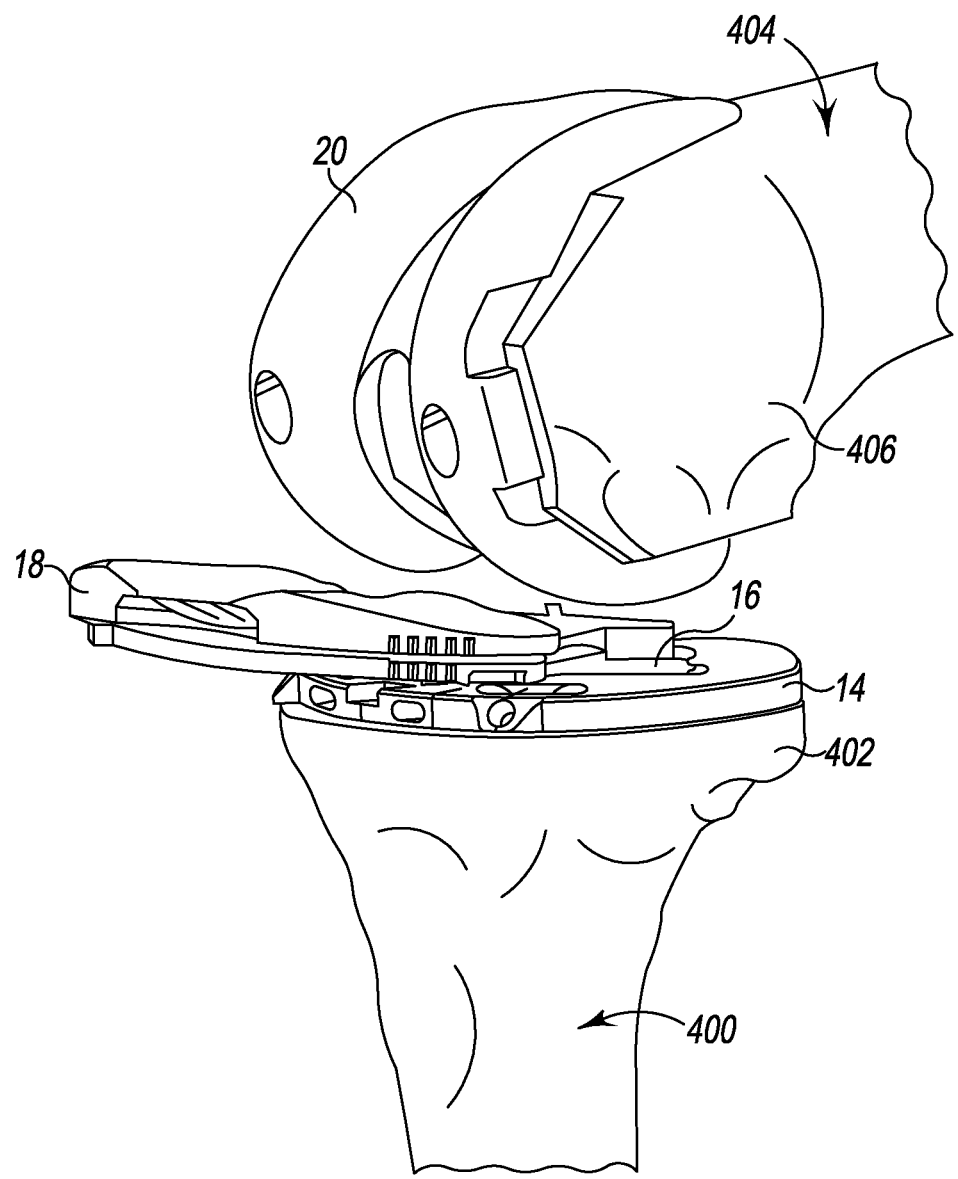
Figure 19:
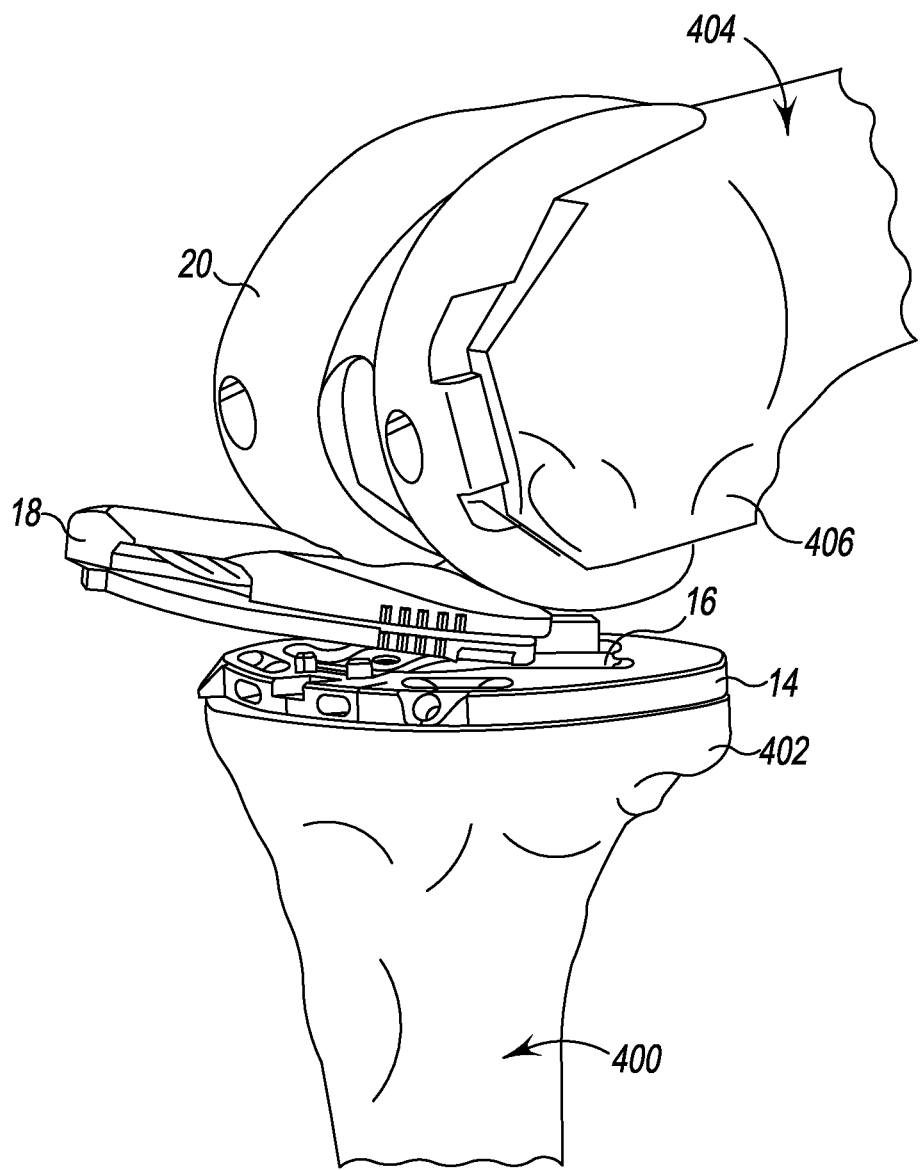
Figure 20:
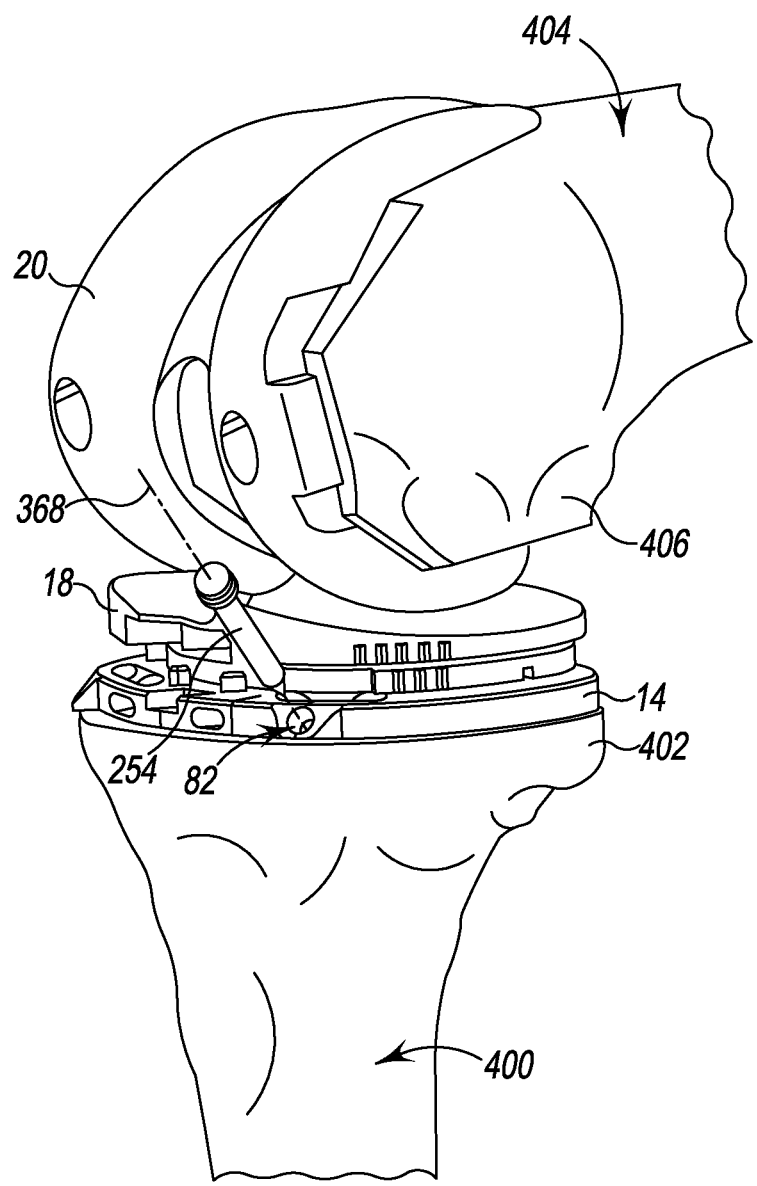

As shown in FIG. 18, the fixed bearing trial component 18 is selected and the surgeon advances the posterior edge 422 of the assembled tibial bearing surface trial component 412 and trial shim 414 into the gap between the tibial base trial component 14 and the femoral trial component 20. The shape of the posterior buttress 170 of the tibial evaluation component 136 allows the fixed bearing trial component 18 to advance in the posterior direction between the tibial base trial component 14 and the femoral trial component 20, as shown in FIGS. 18-19. When the tibial bearing trial component 18 is seated between the tibial base trial component 14 and the femoral trial component 20, the posterior sidewalls 418, 420 of the trial shim 414 engage anterior sidewalls 190, 194 of the arms 172, 174 of the posterior buttress 170 of the tibial evaluation component 136, respectively.

When the fixed bearing trial component 18 is in place, the surgeon may perform the trial reduction. In doing so, the surgeon uses the system 10 to evaluate and check the stability and kinematics of the patient's femur 404 and tibia 400 for implantation of a fixed bearing knee prosthesis or a mobile bearing knee prosthesis. Particularly, the surgeon carefully extends the knee of the patient, noting the anteroposterior stability, medial-lateral stability, and overall alignment in the anterior-posterior plane and medial-lateral plane. Rotational alignment of the tibial base trial component 14 relative to the femoral trial component 20 may be adjusted with the knee in full extension. The rotation of the tibial base trial component 14 is usually centered on the junction between the medial and central one-third of a tibial tubercle.

As the range of motion is evaluated, a load on the femoral trial component 20 translates posteriorly as the knee is moved between extension and flexion. To improve performance, the surgeon may remove the tibial bearing trial component 18 from the tibial base trial component 14 to exchange the trial shim 414 and/or the tibial bearing surface trial component 412. A removal tool (not shown) may be used to detach the tibial bearing trial component 18 from the tibial base trial component 14. The surgeon may use a separator tool (not shown) to detach the trial shim 414 from the tibial bearing surface trial component 412. The surgeon may then select another trial shim 414 having a different thickness or choose a tibial bearing surface trial component 412 with an alternative configuration, for example, a tibial bearing surface trial component 412 that is cruciate retaining or posterior stabilized. The surgeon may continue to try various combinations of trial shim 414 and tibial bearing surface trial component 412 to ascertain which final implant will have the best stability in flexion and extension while permitting full extension. Once the revised combination of trial shim 414 and tibial bearing surface trial component 412 is selected, the two components are assembled to one another and anteriorly advanced in the gap between tibial base trial component 14 and the femoral trial component 20 in the manner previously discussed.

Once the surgeon is satisfied with the trial reduction, without removing any of the trial components 12, the surgeon may inferiorly advance the fixation pin 254 through one of the pinholes 82 of the tibial base trial component 14 and into the proximal end 402 of the patient's tibia 400. As described above, the anterior fixation pinhole 82 is positioned in the center of the inclined surface 102 of the anterior tab 100 of the tibial base trial component 14. The anterior tab 100 extends from the anterior aspect 62 of the tibial base trial component 14, such that the anterior tabs 100 project outward from an anterior edge of the proximal end 402 of the patient's tibia 400, as shown in FIG. 18. The projected anterior tab 100 is exposed throughout the trial reduction process to allow the surgeon to secure the anterior fixation pin 254 in the proximal end 402 of the patient's tibia 400 while the tibial bearing trial components 18 and the femoral trial component 20 remain positioned on the tibial base trial component 14.

Unlike the posterior fixation pinhole 80, the anterior fixation pinhole 82 is not positioned directly perpendicular to the proximal surface of the patient's tibia 400. Because an inferior surface 58 of the anterior tab 100 extends anteriorly outward from the anterior edge of the proximal end 402 of the patient's tibia 400, an anterior portion of the inferior surface 58 does not contact the proximal end 402 of the patient's tibia 400. Accordingly, an inferior opening (not shown) of the anterior fixation pinhole 82 does not wholly rest on the proximal end 402 of the patient's tibia 400. In order to secure the anterior fixation pin 254 in the proximal end 402 of the patient's tibia 400, the anterior fixation pinhole 82 is designed so that when the anterior fixation pin 254 is received in the anterior fixation pinhole 82, the longitudinal axis 368 of the anterior fixation pin 254 is positioned at oblique angles relative to the anterior surface of the proximal end 402 of the patient's tibia. The position of the anterior fixation pinhole 82 allows the anterior fixation pin 254 to advance into the proximal end 402 of the patient's tibia 400 to further secure the tibial base trial component 14 on the proximal end 402 of the patient's tibia 400. After performance of the trial reduction, the surgeon may then continue surgical preparation of the proximal end 402 of the patient's tibia 400.

Figure 21:
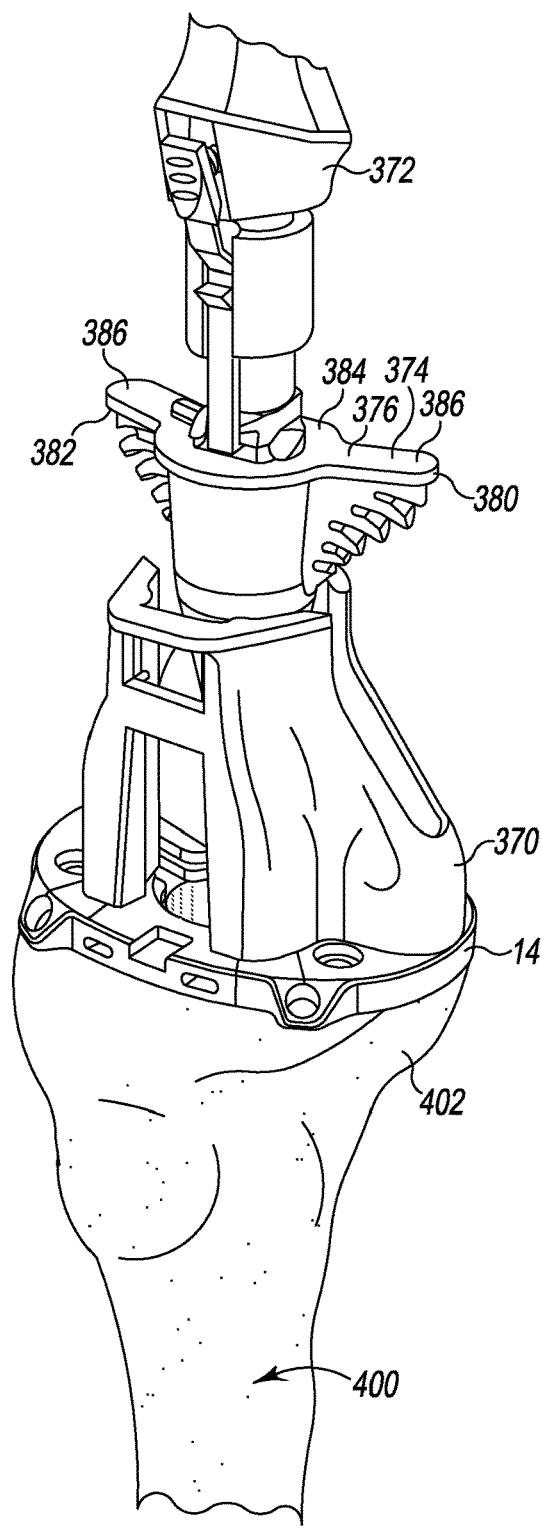

Subsequently, the surgeon may utilize the keel punch 374 seated on the tibial base trial component 14 in the proximal end 402 of the patient's tibia 400 to enlarge the opening in the patient's tibia 400, as shown in FIG. 21. With the tibial base trial component 14 and a guide tower 370 are positioned on the proximal end 402 of the patient's tibia 400, the surgeon may use the tibial base trial component 14 and the guide tower 370 to guide, for example, a surgical drill (not shown) while reaming the proximal end 402 of the patient's tibia 400. Thereafter, the keel punch 374 may be impacted into the proximal end 402 of the patient's tibia 400 before the guide tower 370 is removed, as shown in FIG. 21.

The keel punch 374 is configured to be inserted through the central opening 40 of the tibial base trial component 14 into the proximal end 402 of the patient's tibia 400 to prepare the patient's tibia 400 for a prosthetic component. The keel punch 374 has a base plate 376 having a peripheral rim 380 defined therein. The rim 380 has an inferior surface 382 configured to engage the shelf surface 54 of the tibial base trial component 14 when the keel punch 374 is seated on the tibial base trial component 14. The base plate 376 also includes a central platform 384 sized to be received in the central opening 40 of the tibial base trial component 14, along with a pair of prongs 386 that extend laterally outward from the central platform 384. The prongs 386 are sized to be received in the elongated openings 42 of the tibial base trial component 14. An exemplary procedure for reaming the patient's tibia 400 and installing the keel punch 374 is set forth in U.S. patent application Ser. No. 13/530,945, entitled "METHOD OF SURGICALLY PREPARING A TIBIA FOR IMPLANTATION OF A PROSTHETIC COMPONENT" filed by David Waite et al. and filed on Jun. 28, 2012, which is incorporated herein by reference.

When the keel punch 374 is impacted into and removed from the proximal end 402 of the patient's tibia 400, the resulting proximal end 402 of the patient's tibia 400 includes an opening 408, as shown in FIG. 22. The surgeon may again repeat the trial reduction by assembling the fixed bearing trial component 18 or the mobile bearing trial component 18. This time, the surgeon may use the tibial evaluation component 138, 134 with the sleeve 160, such that the sleeve 160 is received in the opening 408 of proximal end 402 of the patient's tibia 400. For example, the surgeon may choose to assemble one of the trial shims 414 with one of the fixed bearing surface trial components 412 to form a fixed bearing trial component 18. The surgeon then positions the sleeve 160 of the tibial evaluation component 138 into the opening 408 of proximal end 402 of the patient's tibia 400. The surgeon subsequently places the fixed bearing trial component 18 over the tibial base trial component 14, such that the post 126 is received in the central passageway 416 of the trial shim 414 and the posterior sidewalls 418, 420 of the trial shim 414 engages anterior sidewalls 190, 194 of the arms 172, 174 of the posterior buttress 170 of the tibial evaluation component 138, respectively.

The surgeon may then repeat the trial reduction until satisfied with the alignment and the stability of the knee. When the additional trial reduction is complete, the surgeon may use the impaction handle 372 to remove the keel punch 374 from the patient's tibia 400. The surgeon may further use the pin extraction tool 300 to extract the posterior fixation pin 252 and/or the anterior fixation pin 254 from the patient's tibia 400. The resultant features surgically formed in the proximal end 402 of the patient's tibia 400 are configured to receive a tibial tray of a fixed bearing knee prosthesis or a mobile bearing knee prosthesis. The surgeon then completes the surgical procedure of the remaining components of the prosthesis.

Alternatively or additionally, as shown in FIG. 22, the surgeon may choose to assemble one of the trial shims 414 with one of the mobile bearing surface trial components 412 to form a mobile bearing trial component 18. The surgeon may then position the sleeve 160 of the tibial evaluation component 134 into the opening 408 of proximal end 402 of the patient's tibia 400 and place the mobile bearing trial component 18 over the tibial base trial component 14. The surgeon may then move the patient's leg between flexion and extension to evaluate the range of motion. As described above, the configuration of the evaluation component 134 permits the mobile bearing trial component 18 to rotate relative to the patient's tibia as the leg is moved between flexion and extension. It should be appreciated that in other embodiments the trial shim 414 may be positioned on the tibial base trial 14 prior to attaching the bearing surface trial 412 thereto.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system for use during a surgical procedure to implant an orthopaedic knee prosthesis, comprising:
    a tibial base trial component including (i) a superior surface, (ii) an inferior surface positioned opposite the superior surface that is adapted to be positioned on a surgically-prepared proximal end of a patient's tibia, (iii) an opening being defined by an inner wall extending inwardly from the superior surface to a shelf surface positioned between the superior surface and the inferior surface and surrounding a passageway extending through the tibial base trial component, and (iv) a number of fixation pinholes extending through a posterior section of the shelf surface and the inferior surface of the tibial base trial component, an insert component shaped to be received in the opening defined in the tibial base trial component, the insert component comprising a base plate, and a generally Y-shaped posterior buttress extending upwardly from a superior surface of the base plate, and a tibial bearing trial component having an inner sidewall that defines an opening therein, wherein the generally Y-shaped posterior buttress of the insert component is configured to be received in the opening of the tibial bearing trial component to prevent rotation of the tibial bearing trial component relative to the tibial base trial component.

2. The orthopaedic surgical instrument system of claim 1, wherein the posterior buttress includes a post positioned adjacent to a posterior edge of the base plate and a pair of arms extending posteriorly from the post and outwardly from the posterior edge of the base plate.

3. The orthopaedic surgical instrument system of claim 2, wherein:

the pair of arms includes a first arm and a second arm, and a first imaginary line extends along a lateral-most edge of the first arm of the posterior buttress, a second imaginary line extends along a medial-most edge of the second arm of the posterior buttress and intersects the first imaginary line to define an angle of intersection therebetween, the angle of intersection being between 45-145°.

4. The orthopaedic surgical instrument system of claim 1, The orthopaedic surgical instrument system of claim 1, further comprising a retention mechanism to secure the insert component to the tibial base trial component.

5. The orthopaedic surgical instrument system of claim 4, wherein the retention mechanism comprises:

an annular rim extending outwardly from the base plate of the insert component, and a groove defined in the tibial base trial component sized to receive the annular rim of the insert component.

6. The orthopaedic surgical instrument system of claim 1, wherein the insert component includes a first prong extending medially from the base plate and a second prong extending laterally from the base plate.

7. The orthopaedic surgical instrument system of claim 1, further comprising a fixation pin including:

a head including (i) an inferior surface configured to engage the posterior section of the shelf surface and (ii) a superior surface positioned opposite the inferior surface, and a shaft extending from the inferior surface of the head, wherein when the inferior surface of the head of the fixation pin is engaged with the posterior section of the shelf surface, the superior surface of the head of the fixation pin is configured to be positioned at or below an imaginary plane defined by the superior surface of the tibial base trial component and the shaft is sized to extend inferiorly from at least one of the fixation pinholes defined in the tibial base trial component.

8. The orthopaedic surgical instrument system of claim 7, further comprising:

a pin extraction tool comprising (i) a handle, (ii) a pivoting member pivotally coupled to the handle, and (iii) a receiving end including a first jaw extending from the handle and a second jaw extending from the pivoting member, the first jaw and the second jaw being configured to engage the head of the fixation pin, wherein the pivoting member is pivotable between (i) a closed position in which the first jaw and the second jaw define a pocket sized to retain the head of the fixation pin, and (ii) an open position in which the first jaw and the second jaw are spaced apart to permit the head of the fixation pin to be disengaged from the first jaw and the second jaw.

9. The orthopaedic surgical instrument system of claim 1, wherein the insert component is a first insert component, and the system further comprises a second insert component configured to be separately received in the opening defined in the tibial base trial component in place of the first insert component, the second insert component having a central post, wherein a superior surface of the central post has a ramp surface defined therein, the ramp surface inclines superiorly in an anterior-to-posterior direction.

10. The orthopaedic surgical instrument system of claim 1, wherein the insert component further comprises an anterior buttress extending outwardly from an anterior edge of the base plate.

11. The orthopaedic surgical instrument system of claim 10, wherein the anterior buttress of the insert component includes (i) a pair of arms extending anteriorly from the anterior edge of the base plate and (ii) a tab extending superiorly from an anterior end of each arm.

12. The orthopaedic surgical instrument system of claim 1, wherein the insert component is a first insert component of a plurality of insert components, each insert component being shaped to be separately received in the opening defined in the tibial base trial component, wherein a number of the insert components include a base plate and a keel extending inferiorly from the base plate.

13. The orthopaedic surgical instrument system of claim 12, wherein the keel includes a pair of spikes extending inferiorly from the base plate.

* * * * *